United States Patent
Vasei

(10) Patent No.: US 10,392,408 B2
(45) Date of Patent: Aug. 27, 2019

(54) SILOXANE OLIGOMERS FOR THE TREATMENT OF SOLID SURFACES

(71) Applicant: AVMOR LTD, Laval (CA)

(72) Inventor: Mitra Vasei, Montreal (CA)

(73) Assignee: AVMOR LTD, Laval (CA)

(*) Notice: Subject to any disclaimer, the term of this patent is extended or adjusted under 35 U.S.C. 154(b) by 0 days.

(21) Appl. No.: 16/018,823

(22) Filed: Jun. 26, 2018

(65) Prior Publication Data

US 2018/0370994 A1    Dec. 27, 2018

Related U.S. Application Data

(60) Provisional application No. 62/525,355, filed on Jun. 27, 2017.

(51) Int. Cl.
   *C07F 7/12*    (2006.01)
   *C08G 77/00*   (2006.01)

(52) U.S. Cl.
   CPC .............. *C07F 7/126* (2013.01); *C08G 77/00* (2013.01)

(58) Field of Classification Search
   None
   See application file for complete search history.

(56) References Cited

U.S. PATENT DOCUMENTS

| | | | |
|---|---|---|---|
| 5,808,125 A | 9/1998 | Standke et al. | |
| 5,849,942 A * | 12/1998 | Standke | C03C 17/30 556/424 |
| 5,885,341 A | 3/1999 | Standke et al. | |
| 6,251,989 B1 | 6/2001 | Edelmann et al. | |
| 6,491,838 B1 | 12/2002 | Standke et al. | |
| 6,706,923 B2 | 3/2004 | Haniff et al. | |
| 8,298,679 B2 | 10/2012 | Albert et al. | |
| 8,349,911 B2 | 1/2013 | Kuehnle | |
| 2009/0198000 A1 | 8/2009 | Weinelt et al. | |
| 2010/0159144 A1 | 6/2010 | Standke et al. | |
| 2011/0268899 A1 | 11/2011 | Albert et al. | |
| 2016/0244638 A1 | 8/2016 | Ozaki et al. | |

FOREIGN PATENT DOCUMENTS

| | | | |
|---|---|---|---|
| EP | 0675128 B1 | 12/2001 | |
| EP | 1178071 B1 | 8/2006 | |
| WO | 2005014741 A1 | 2/2005 | |
| WO | 2006010388 A1 | 2/2006 | |
| WO | 2006010666 A1 | 2/2006 | |
| WO | 2010114111 A1 | 10/2010 | |

OTHER PUBLICATIONS

Bain, Colin D., Graham D. Burnett-Hall, and Richard R. Montgomerie. "Rapid motion of liquid drops." Nature 372.6505 (1994): 414.
CAS entry No. 1011795.61.1—Dynasylan F 8815.
Chakraborty, Monojit, et al. "Thermally enhanced self-propelled droplet motion on gradient surfaces." RSC Advances 5.56 (2015): 45266-45275.
Chaudhury, Manoj K., and George M. Whitesides. "How to make water run uphill." No. TR-48. Harvard Univ Cambridge MA Dept of Chemistry, 1992.
Dos Santos, Fabrice Domingues, and Thierry Ondarcuhu. "Free-running droplets." Physical Review Letters 75.16 (1995): 2972.
Dynasylan Product Range, Brochure by Evonik Industries, revised Jul. 1, 2016.
Izri, Ziane, et al. "Self-propulsion of pure water droplets by spontaneous nnarangoni-stress-driven motion." Physical review letters 113.24 (2014): 248302.
Product Information Dynasylan F 8815, Brochure by Evonik Resource GmbH, dated Aug. 2016.
Safety Data Sheet—Dynasylan F 8815.
Sumino, Yutaka, and Kenichi Yoshikawa. "Self-motion of an oil droplet: A simple physicochemical model of active Brownian motion." Chaos: An Interdisciplinary Journal of Nonlinear Science 18.2 (2008): 026106.
Yao, Xi, et al. "Running droplet of interfacial chemical reaction flow." Soft Matter 8.22 (2012): 59885991.

* cited by examiner

*Primary Examiner* — Clinton A Brooks
*Assistant Examiner* — Kofi Adzamli
(74) *Attorney, Agent, or Firm* — Isabelle Pelletier

(57) ABSTRACT

A siloxane oligomer of the following formula is provided. This siloxane can increase the hydrophobicity and/or the lipophobicity of a surface of a solid substrate and/or self-propel when deposited in solution on a surface of a solid substrate.

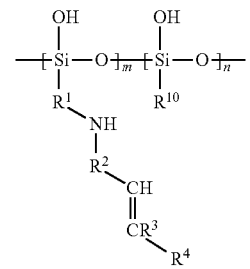

20 Claims, 15 Drawing Sheets

SILOXANE OLIGOMERS FOR THE TREATMENT OF SOLID SURFACES

CROSS REFERENCE TO RELATED APPLICATIONS

This application claims benefit, under 35 U.S.C. § 119(e), of U.S. provisional application Ser. No. 62/525,355, filed on Jun. 27, 2017. All documents above are incorporated herein in their entirety by reference.

FIELD OF THE INVENTION

The present invention relates to siloxane oligomers, preferably water-soluble siloxane oligomers. More specifically, the present invention is concerned with such oligomers useful for increasing the hydrophobicity and/or lipophobicity of solid surfaces, and/or which can self-propel when deposited in solution, especially in water, on a solid surface.

BACKGROUND OF THE INVENTION

It is desirable in various applications to confer hydrophobicity and/or lipophobicity to a surface of a solid substrate. Fluorosilane oligomers, such as water-born Evonik's Dynasylan® F8815, are effective for altering, temporarily or permanently, the hydrophobicity and/or lipophobicity of the surface of a wide range of substrates such as glass, wood, concrete and fabrics. However, the low solubility in water of most commercial fluorosilane oligomers means that they are mostly sold and used dissolved in a non-aqueous organic solvent. This brings significant restrictions on these products' applications because of transfer regulations, environmental hazards and health concerns.

On another subject, self-propulsion of a liquid occurs when a surface tension gradient causes the liquid to flow, for example against the gravitational force. Indeed, a difference in surface tension on either side of a liquid droplet produces a directional transport of the droplet through a second liquid or over a solid substrate. This phenomenon is known as the chemical Marangoni effect.

A classic example is wine, which may exhibit a visible effect called "tears" on the wall of a glass, as shown in FIG. 1A. This effect is due to the fact that alcohol has a lower surface tension and higher volatility than water. The water/alcohol solution (i.e. wine) first rises on the surface of the glass due to capillary action. Then, the alcohol evaporates from the film leaving behind a liquid with a higher surface tension (because it contains more water and less alcohol). This region with a lower concentration of alcohol (greater surface tension) pulls on the surrounding fluid more strongly than the regions with a higher alcohol concentration (lower in the glass), see FIG. 1B. As a result, the liquid is pulled up until its own weight exceeds the force of the Marangoni effect, and the liquid drips back down the vessel's walls. The Marangoni effect can also be easily demonstrated by spreading a thin film of water on a smooth surface and then allowing a drop of alcohol to fall on the center of the film. The liquid will rush out of the region where the drop of alcohol fell.

In artificial systems, a similar effect can be achieved for a droplet sitting on a homogeneous surface if the droplet contains a species which adsorbs onto the surface. Droplet motion is then driven by the irreversible modification of the surface free energy which affects the interfacial energy on either side of the droplet—a so-called "chemical" Marangoni effect. The energy released by chemical reactions with the surface that cause the droplet of liquid to move across the surface and even up a non-horizontal surface.

The self-propulsion of liquid droplets on solid surfaces has attracted broadening attention for decades. This droplet motion system can be an exceptional model of the process of chemo-mechanical energy conversion. However, all the reported "chemical Marangoni" effects observed with fluoro-organosilanes are for driving oil droplets. Limited by the critical micelle concentration and organo-silanes solubility in water, it is difficult to produce self-propelling water droplets. Thus, it remains challenging to develop an aqueous self-propelling system.

SUMMARY OF THE INVENTION

In accordance with the present invention, there is provided:
1. A siloxane oligomer of formula:

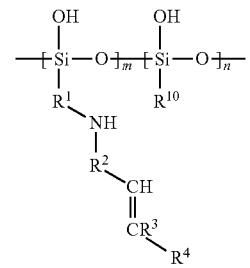

wherein:
R$^1$ is alkylene optionally interrupted with one or more —NR$^{20}$- group;
R$^2$ is alkylene;
R$^3$ is —H, —F or optionally substituted alkyl;
R$^4$ is alkyl or fluoroalkyl;
R$^{10}$ is fluoroaryl or alkyl optionally substituted, preferably end-substituted, by:
fluoroalkyl,
glycidyloxy,
optionally substituted aryl,
optionally substituted aryloxy, or
—N$^+$(R$^{21}$)(R$^{22}$)(R$^{23}$);
R$^{20}$ is H or alkyl;
R$^{21}$, R$^{22}$ and R$^{23}$ are independently alkyl, optionally substituted aryl, or alkyl-O-alkyl; and
m and n represent the number of repeat units, m being 1 or greater and n being 0 or greater.
2. The oligomer of item 1, wherein n is 0.
3. The oligomer of item 1, wherein n is 1 or greater.
4. The oligomer of item 2, wherein the m:n ratio varies between about 1:100 and about 100:1, preferably between about 1:1 and about 100:1, and more preferably between about 10:1 and about 100:1.
5. The oligomer of any one of items 1 to 4, wherein the alkylene in R$_1$ is a C$_{1-12}$, C$_{2-12}$, C$_{3-12}$, C$_{1-10}$, C$_{2-10}$, C$_{3-10}$, C$_{1-8}$, C$_{2-8}$C$_{3-8}$, C$_{1-7}$, C$_{2-7}$, or C$_{3-7}$ alkylene.
6. The oligomer of any one of items 1 to 5, wherein R$^1$ is uninterrupted alkylene or alkylene interrupted by one or two —NR$^{20}$—.
7. The oligomer of any one of items 1 to 6, wherein R$^1$ is -alkylene-, -alkylene-NR$^{20}$-alkylene-, or -alkylene-NR$^{20}$-alkylene-NR$^{20}$-alkylene-.
8. The oligomer of any one of items 1 to 7, wherein R$^{20}$ is H.

9. The oligomer of any one of items 1 to 8, wherein $R^1$ is -alkylene-, -alkylene-NH-alkylene-, or -alkylene-NH-alkylene-NH-alkylene-, wherein preferably each alkylene is a $C_{1-6}$, $C_{1-5}$, $C_{1-4}$, $C_{1-3}$, $C_{2-6}$, $C_{2-5}$, $C_{2-4}$, or $C_{2-3}$ alkylene, and more preferably each alkylene is a $C_2$ or $C_3$ alkylene.

10. The oligomer of any one of items 1 to 9, wherein $R^1$ is -propylene-, *-propylene-NH-ethylene-, or *-propylene-NH-ethylene-NH-ethylene-, the star (*) indicating the point of attachment to the Si atom.

11. The oligomer of any one of items 1 to 10, wherein $R^1$ is -propylene- or *-propylene-NH-ethylene-NH-ethylene-, the star (*) indicating the point of attachment to the Si atom.

12. The oligomer of any one of items 1 to 11, wherein the alkylene in $R^2$ is a $C_{1-6}$, $C_{1-5}$, $C_{1-4}$, $C_{1-3}$, $C_{1-2}$, or $C_1$ alkylene.

13. The oligomer of any one of items 1 to 12, wherein $R^2$ is methylene.

14. The oligomer of any one of items 1 to 13, wherein alkyl in $R^3$ is optionally substituted with fluoroalkyl, preferably perfluoroalkyl.

15. The oligomer of any one of items 1 to 14, wherein $R^3$ is —H or —F.

16. The oligomer of any one of items 1 to 15, wherein $R^3$ is —F.

17. The oligomer of any one of items 1 to 16, wherein the alkyl in $R^4$ is a $C_{1-12}$, $C_{2-12}$, $C_{3-12}$, $C_{1-10}$, $C_{2-10}$, $C_{3-10}$, $C_{1-8}$, $C_{2-8}$, $C_{3-8}$, $C_{1-7}$, $C_{2-7}$, or $C_{3-7}$ alkyl, more preferably a $C_3$ or $C_7$ alkyl.

18. The oligomer of any one of items 1 to 17, wherein the fluoroalkyl in $R^4$ is a $C_{1-12}$, $C_{2-12}$, $C_{3-12}$, $C_{1-10}$, $C_{2-10}$, $C_{3-10}$, $C_{1-8}$, $C_{2-8}$, $C_{3-8}$, $C_{1-7}$, $C_{2-7}$, or $C_{3-7}$ fluoroalkyl, more preferably a $C_3$ or $C_7$ fluoroalkyl.

19. The oligomer of any one of items 1 to 18, wherein $R^4$ is fluoroalkyl, more preferably perfluoroalkyl.

20. The oligomer of any one of items 1 to 19, wherein $R^4$ is $C_3$perfluoroalkyl or $C_7$perfluoroalkyl.

21. The oligomer of any one of items 1 to 20, wherein the fluoroaryl in $R^{10}$ is perfluoroaryl.

22. The oligomer of any one of items 1 to 21, wherein the fluoroaryl in $R^{10}$ is fluorophenyl, preferably perfluorophenyl.

23. The oligomer of any one of items 1 to 22, wherein the aryl that substitutes the alkyl in $R^{10}$ is phenyl.

24. The oligomer of any one of items 1 to 23, wherein the aryl that substitutes the alkyl in $R^{10}$ is optionally substituted with fluoroaryl, preferably perfluoroaryl.

25. The oligomer of any one of items 1 to 24, wherein the aryl that substitutes the alkyl in $R^{10}$ is unsubstituted.

26. The oligomer of any one of items 1 to 25, wherein the aryl that substitutes the alkyl in $R^{10}$ is phenyl.

27. The oligomer of any one of items 1 to 26, wherein the aryloxy that substitutes the alkyl in $R^{10}$ is optionally substituted with hydroxy or carbonyl, preferably hydroxy.

28. The oligomer of any one of items 1 to 27, wherein the aryloxy that substitutes the alkyl in $R^{10}$ is substituted with hydroxy or carbonyl, preferably hydroxy.

29. The oligomer of any one of items 1 to 28, wherein the aryloxy that substitutes the alkyl in $R^{10}$ is benzophenonyloxy, preferably benzophenonyl-4-oxy.

30. The oligomer of item 29, wherein the benzophenonyloxy or benzophenonyl-4-oxy is substituted by one or more hydroxy group(s), more preferably by a single hydroxy group, more preferably at position 2.

31. The oligomer of any one of items 1 to 30, wherein the aryloxy is 2-hydroxybenzophenonyl-4-oxy.

32. The oligomer of any one of items 1 to 31, wherein the alkyl in $R^{10}$ is $C_{2-12}$alkyl.

33. The oligomer of any one of items 1 to 32, wherein, when unsubstituted, the alkyl in $R^{10}$ is a $C_{4-12}$, $C_{6-12}$, $C_{8-12}$, $C_{4-10}$, $C_{6-10}$, $C_{8-10}$, $C_{4-8}$, $C_{6-8}$, or $C_8$alkyl.

34. The oligomer of any one of items 1 to 33, wherein, when substituted, the alkyl in $R^{10}$ is a $C_{1-6}$, $C_{1-5}$, $C_{1-4}$, $C_{1-3}$, $C_{2-6}$, $C_{2-5}$, $C_{2-4}$, or $C_{2-3}$ alkyl.

35. The oligomer of any one of items 1 to 34, wherein, when substituted by fluoroalkyl, the alkyl in $R^{10}$ is a $C_2$alkyl.

36. The oligomer of any one of items 1 to 35, wherein, when substituted by glycidyloxy, the alkyl in $R^{10}$ is a $C_3$alkyl.

37. The oligomer of any one of items 1 to 36, wherein the fluoroalkyl optionally substituting the alkyl in $R^{10}$ is a $C_{4-14}$, $C_{4-12}$, $C_{4-10}$, $C_{6-14}$, $C_{6-12}$, $C_{6-10}$, $C_{8-14}$, $C_{8-12}$, or $C_{8-10}$ alkyl, preferably a $C_{8-10}$fluoroalkyl.

38. The oligomer of any one of items 1 to 37, wherein the fluoroalkyl optionally substituting the alkyl in $R^{10}$ is perfluoroalkyl.

39. The oligomer of any one of items 1 to 38, wherein the alkyl is $R^{21}$, $R^{22}$ and $R^{23}$ is $C_{4-12}$, $C_{6-12}$, $C_{8-12}$, $C_{4-10}$, $C_{6-10}$, $C_{8-10}$, $C_{4-8}$, $C_{6-8}$, or $C_8$alkyl.

40. The oligomer of any one of items 1 to 39, wherein each of the alkyl groups in the alkyl-O-alkyl in $R^{21}$, $R^{22}$ and $R^{23}$ is $C_{4-12}$, $C_{6-12}$, $C_{8-12}$, $C_{4-10}$, $C_{6-10}$, $C_{8-10}$, $C_{4-8}$, $C_{6-8}$, or $C_8$alkyl.

41. The oligomer of any one of items 1 to 40, wherein the aryl in $R^{21}$, $R^{22}$ and $R^{23}$ is phenyl.

42. The oligomer of any one of items 1 to 41, wherein the aryl in $R^{21}$, $R^{22}$ and $R^{23}$ is optionally substituted with a fluoride atom, alkyl or alkoxy.

43. The oligomer of any one of items 1 to 42, wherein the alkyl optionally substituting the aryl in $R^{21}$, $R^{22}$ and $R^{23}$ is a $C_{1-6}$, $C_{1-5}$, $C_{1-4}$, $C_{1-3}$, $C_{2-6}$, $C_{2-5}$, $C_{2-4}$, or $C_{2-3}$ alkyl.

44. The oligomer of any one of items 1 to 43, wherein the alkoxy optionally substituting the aryl in $R^{21}$, $R^{22}$ and $R^{23}$ is a $C_{1-6}$, $C_{1-5}$, $C_{1-4}$, $C_{1-3}$, $C_{2-6}$, $C_{2-5}$, $C_{2-4}$, or $C_{2-3}$ alkoxy.

45. The oligomer of any one of items 1 to 44, wherein the aryl in $R^{21}$, $R^{22}$ and $R^{23}$ is unsubstituted.

46. The oligomer of any one of items 1 to 45, wherein $R^{10}$ is 1H,1H,2H,2H-perfluorooctyl, 1H,1H,2H,2H-perfluorodecyl, 3,3,3-trifluoropropyl, pentafluorophenyl, octyl, or 3-glycidyloxypropyl.

47. The oligomer of any one of items 1 to 46, wherein $R_{10}$ is unsubstituted alkyl or alkyl substituted with fluoroalkyl, preferably perfluoroalkyl.

48. The oligomer of any one of items 1 to 47, wherein $R^{10}$ is 1H,1H,2H,2H-perfluorooctyl, 1H,1H,2H,2H-perfluorodecyl, 3,3,3-trifluoropropyl, or octyl.

49. The oligomer of any one of items 1 to 48, wherein $R^{10}$ is 1H,1H,2H,2H-perfluorooctyl, 1H,1H,2H,2H-perfluorodecyl, or octyl.

50. The oligomer of any one of items 1 to 49, being:

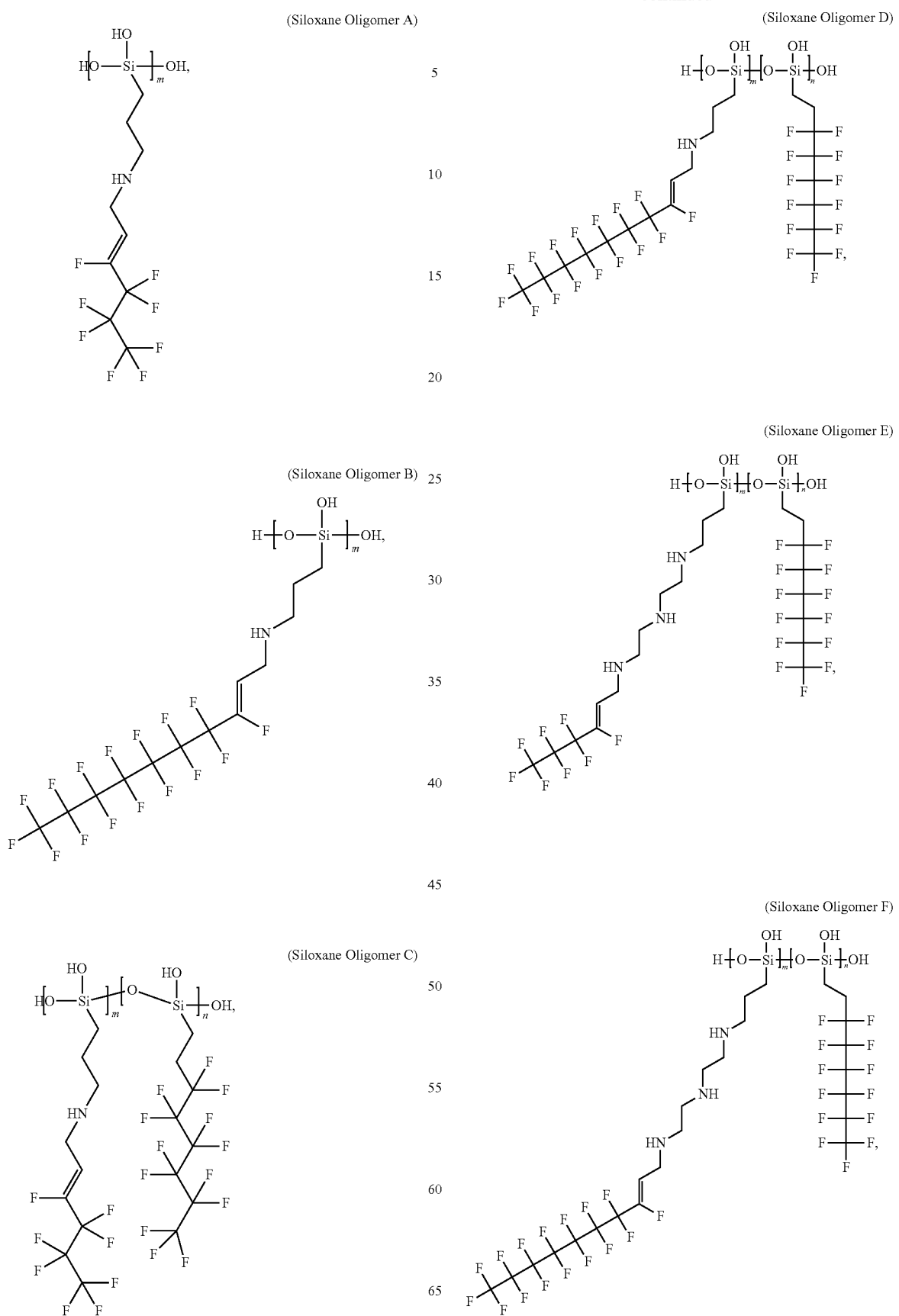

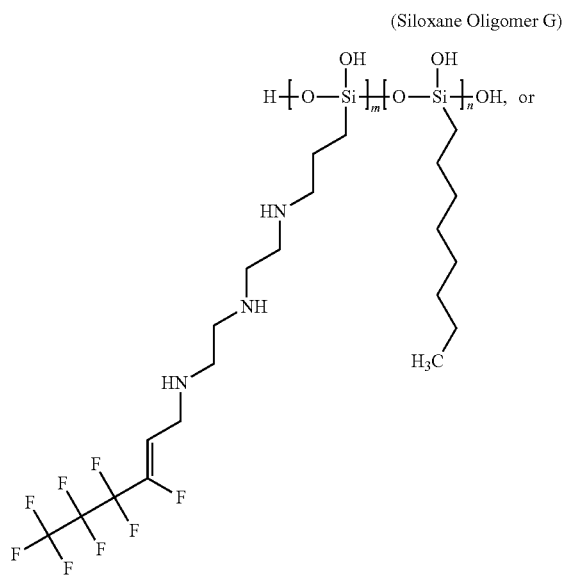
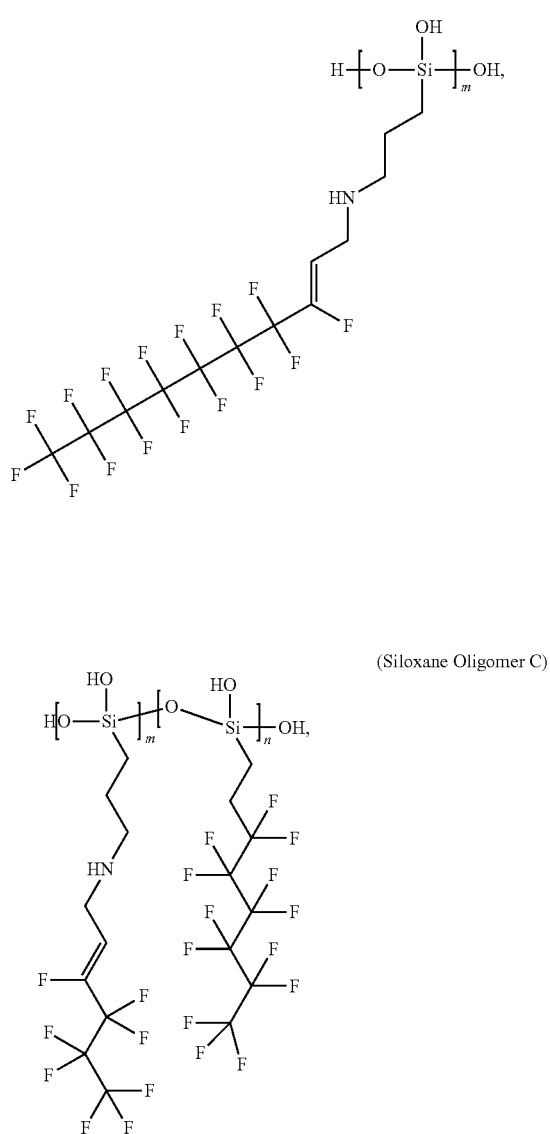
51. The oligomer of any one of items 1 to 50, being:
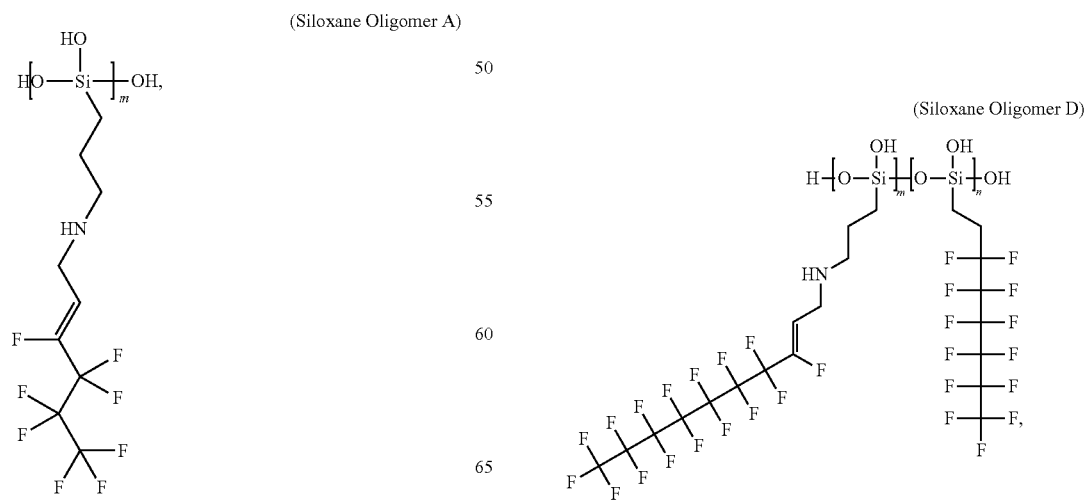

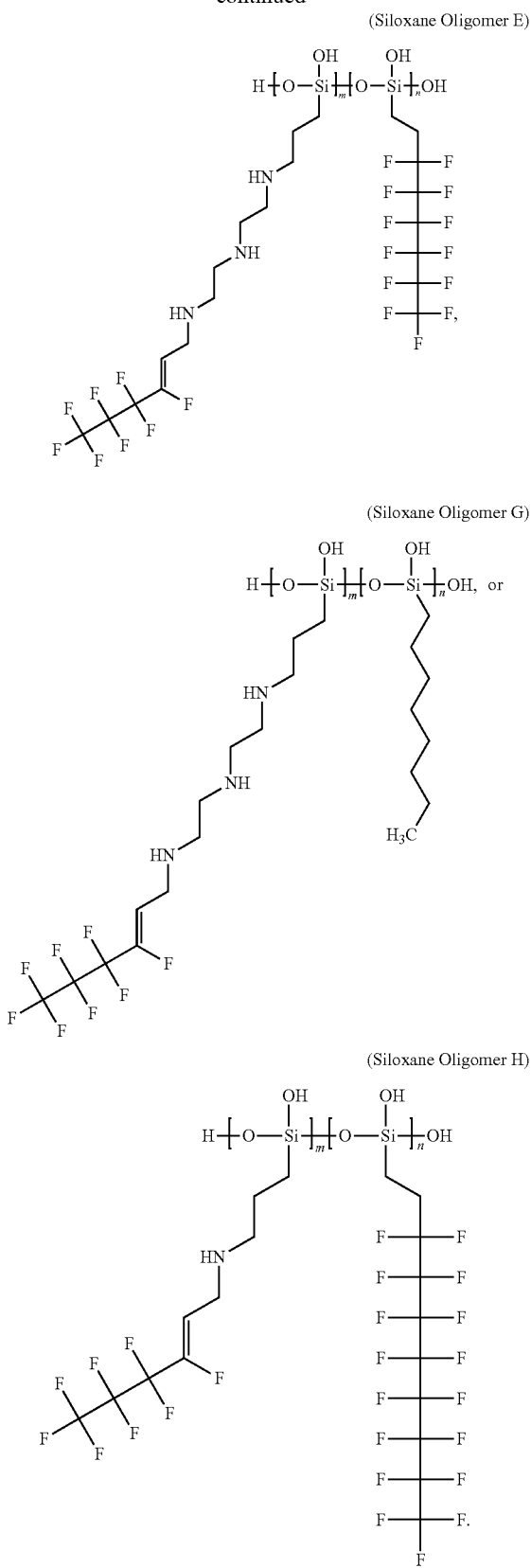

52. The siloxane oligomer of any one of items 1 to 51 being water-soluble.

53. Use of the siloxane oligomer of any one of items 1 to 52 for increasing the hydrophobicity and/or the lipophobicity of a surface of a solid substrate.

54. Use of the siloxane oligomer of any one of items 1 to 52 for forming a hydrophobic and/or lipophobic coating on a surface of a solid substrate.

55. The use of item 53 or 54, wherein the surface is a wood, metal, glass, fabric or concrete surface, preferably a glass, fabric or concrete surface, more preferably a glass surface.

56. A method of rendering a surface more hydrophobic and/or more lipophobic, the method comprising the step of applying the siloxane oligomer of any one of items 1 to 52 to the surface.

57. A method of forming a hydrophobic and/or lipophobic coating on a surface, the method comprising the step of contacting the siloxane oligomer of any one of items 1 to 52 with the surface.

58. The method of item 56 or 57, wherein the surface is a wood, metal, glass, fabric or concrete surface, preferably a glass, fabric or concrete surface, more preferably a glass surface.

59. The method of any one of items 56 to 58, further comprising rinsing the surface.

60. The method of any one of items 56 to 59, further comprising drying the surface.

61. A solution of the siloxane oligomer of any one of items 1 to 52.

62. The solution of item 61, being an aqueous solution.

63. Use of the siloxane oligomer of any one of items 1 to 52 for the self-propulsion of a liquid on a surface of a solid substrate.

64. The use of item 63, wherein the surface is a glass surface.

65. The use of item 63 or 64, wherein the liquid is water or an aqueous solution.

66. A method for the self-propulsion of a liquid on a surface of a solid substrate, the method comprising the step of forming a solution of the siloxane oligomer of any one of items 1 to 52 in the liquid, depositing the solution on the surface and allowing the solution to self-propel on the surface.

67. The method of item 66, wherein the surface is a glass surface.

68. The method of item 66 or 67, wherein the liquid is water or an aqueous solution.

DETAILED DESCRIPTION OF THE INVENTION

Siloxane Oligomers

Figure 1A:
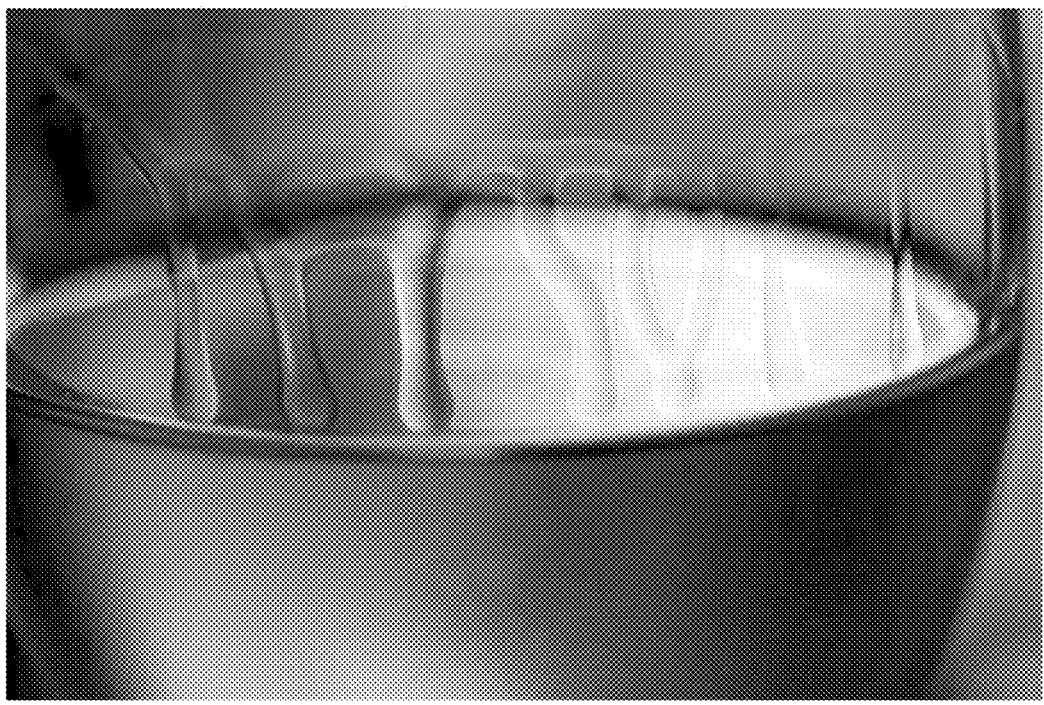
FIG. 1 shows A) tears on the side of a wine glass.
FIG. 1B) shows the regions of higher and lower surface tension on a wine glass wall together with the resulting Marangoni effect.
Figure 1B:
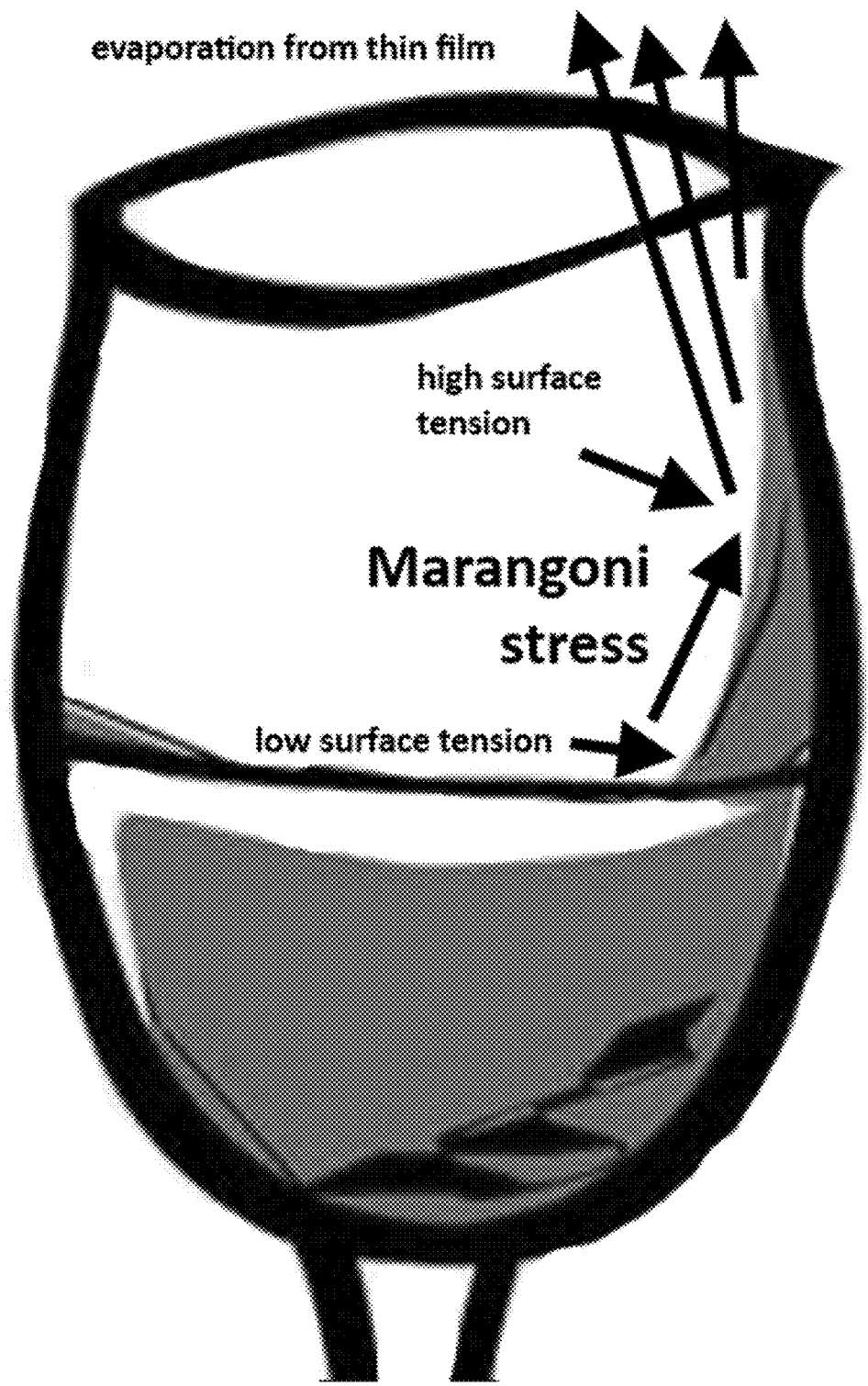

The present invention also relates to a siloxane oligomer of formula:

$$\begin{array}{c} \text{OH} \quad\quad\quad \text{OH} \\ | \quad\quad\quad\quad\quad | \\ -\!\!-\!\!\!\text{Si}\!\!-\!\!\text{O}\!\!\!-\!\!\!\!\!\!{}_m\!\!\!-\!\!\!\text{Si}\!\!-\!\!\text{O}\!\!\!-\!\!\!\!\!\!{}_n\!\!\!- \\ | \quad\quad\quad\quad\quad | \\ R^1 \quad\quad\quad R^{10} \\ \ \ \backslash \\ \ \ \ \text{NH} \\ \quad\ \ | \\ \quad R^2 \\ \quad\quad \backslash \text{CH} \\ \quad\quad\quad \| \\ \quad\quad\quad CR^3 \\ \quad\quad\quad\quad \backslash R^4 \end{array}$$

wherein
R$^1$ is alkylene optionally interrupted with one or more —NR$^{20}$-group;

R$^2$ is alkylene;
R$^3$ is —H, —F or optionally substituted alkyl;
R$^4$ is alkyl or fluoroalkyl;
R$^{10}$ is fluoroaryl or alkyl optionally substituted, preferably end-substituted, by:
 fluoroalkyl,
 glycidyloxy,
 optionally substituted aryl,
 optionally substituted aryloxy, or
 —N$^+$(R$^{21}$)(R$^{22}$)(R$^{23}$);
R$^{20}$ is H or alkyl;
R$^{21}$, R$^{22}$ and R$_{23}$ are independently alkyl, optionally substituted aryl, or alkyl-O-alkyl; and
m and n represent the number of repeat units, m being 1 or greater and n being 0 or greater.

The siloxane oligomers of the invention are characterized by several functional groups: a secondary amine, a double bond, and, in embodiments, a fluoroalkyl, preferably a perfluoroalkyl in R$^4$.

In embodiments, n is 0.

In other embodiments, n is not 0 (i.e. n is 1 or greater). In such embodiments, the m:n ratio (molar ratio) varies between about 1:100 and about 100:1. In preferred embodiments, the ratio is between about 1:1 and about 100:1, preferably between about 10:1 and about 100:1.

In embodiments, the alkylene in R$_1$ is a $C_{1-12}$, $C_{2-12}$, $C_{3-12}$, $C_{1-10}$, $C_{2-10}$, $C_{3-10}$, $C_{1-8}$, $C_{2-8}$, $C_{3-8}$, $C_{1-7}$, $C_{2-7}$, or $C_{3-7}$ alkylene. In embodiments, R$^1$ is uninterrupted alkylene or alkylene interrupted by one or two —NR$^{20}$-groups. In preferred embodiments, R$^1$ is -alkylene-, -alkylene-NR$^{20}$-alkylene-, or -alkylene-NR$^{20}$-alkylene-NR$^{20}$-alkylene-. In preferred embodiments, R$^{20}$ is H. In more preferred embodiments, R$^1$ is -alkylene-, -alkylene-NH-alkylene-, or -alkylene-NH-alkylene-NH-alkylene-. In all the preceding embodiments of R$^1$, each alkylene is preferably and independently a $C_{1-6}$, $C_{1-5}$, $C_{1-4}$, $C_{1-3}$, $C_{2-6}$, $C_{2-5}$, $C_{2-4}$, or $C_{2-3}$alkylene, more preferably each alkylene is independently a $C_2$ or $C_3$ alkylene. In yet more preferred embodiments, R$^1$ is propylene, *-propylene-NH-ethylene-, or *-propylene-NH-ethylene-NH-ethylene-, the star (*) indicating the point of attachment to the Si atom. In most preferred embodiments, R$^1$ is propylene or *-propylene-NH-ethylene-NH-ethylene-, the star (*)indicating the point of attachment to the Si atom.

In embodiments, the alkylene in R$^2$ is a $C_{1-6}$, $C_{1-5}$, $C_{1-4}$, $C_{1-3}$, $C_{1-2}$, or $C_1$alkylene. In preferred embodiments, R$^2$ is methylene.

In embodiments, the optional substituent(s) of the alkyl in R$^3$ is(are) fluoroalkyl, preferably perfluoroalkyl.

In preferred embodiments, R$^3$ is —H or —F, more preferably —F.

In embodiments, the alkyl and the fluoroalkyl in R$^4$ are $C_{1-12}$, $C_{2-12}$, $C_{3-12}$, $C_{1-10}$, $C_{2-10}$, $C_{3-10}$, $C_{1-8}$, $C_{2-8}$, $C_{3-8}$, $C_{1-7}$, $C_{2-7}$, or $C_{3-7}$ alkyl/fluoroalkyl, more preferably $C_3$ or $C_7$ alkyl/fluoroalkyl. In preferred embodiments, R$^4$ is fluoroalkyl, more preferably perfluoroalkyl. In most preferred embodiments, R$^4$ is $C_3$perfluoroalkyl or $C_7$perfluoroalkyl.

In embodiments, the fluoroaryl in R$^{10}$ is perfluoroaryl.

In embodiments, the fluoroaryl in R$^{10}$ is fluorophenyl, preferably perfluorophenyl.

In embodiments, the optional substituent(s) of the aryl (which itself substitutes the alkyl) in R$^{10}$ is(are) fluoroaryl, preferably perfluoroaryl. In preferred embodiments, the aryl is unsubstituted.

In preferred embodiments, the aryl substituting the alkyl in R$^{10}$ is phenyl.

In embodiments, the optional substituent(s) of the aryloxy (which itself substitutes the alkyl) in $R^{10}$ is(are) hydroxy or carbonyl, preferably hydroxy. In preferred embodiment the aryloxy is substituted.

In preferred embodiments, the aryloxy substituting the alkyl in $R^{10}$ is benzophenonyloxy, preferably benzophenonyl-4-oxy

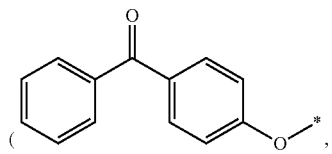 [SMILES: *Oc1ccc(C(=O)c2ccccc2)cc1]

wherein the star (*) denotes the point of attachment to the alkyl). In more preferred embodiments, the benzophenonyloxy or benzophenonyl-4-oxy is substituted by one or more substituents as defined above, preferably by one or more hydroxy group(s), more preferably by a single hydroxy group. In preferred embodiments, this single hydroxy group is at position 2. Thus, in most preferred embodiments, the aryloxy is 2-hydroxybenzophenonyl-4-oxy

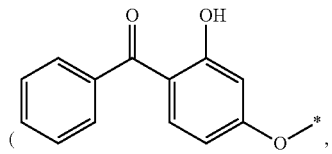 [SMILES: *Oc1ccc(C(=O)c2ccccc2)c(O)c1]

wherein the star (*) denotes the point of attachment to the alkyl).

In embodiments, the alkyl in $R^{10}$ is $C_{2-12}$alkyl.

In preferred embodiments, when unsubstituted, the alkyl in $R^{10}$ is a $C_{4-12}$, $C_{6-12}$, $C_{8-12}$, $C_{4-10}$, $C_{6-10}$, $C_{8-10}$, $C_{4-8}$, $C_{6-8}$, or $C_8$alkyl.

In preferred embodiments, when substituted, the alkyl in $R^{10}$ is a $C_{1-6}$, $C_{1-5}$, $C_{1-4}$, $C_{1-3}$, $C_{2-6}$, $C_{2-5}$, $C_{2-4}$, or $C_{2-3}$ alkyl. In more preferred embodiments, when substituted by fluoroalkyl, the alkyl in $R^{10}$ is a $C_2$alkyl. In other preferred embodiments, when substituted by glycidyloxy, the alkyl in $R^{10}$ is a $C_3$alkyl.

In embodiments, the fluoroalkyl substituting the alkyl in $R^{10}$ is a $C_{4-14}$, $C_{4-12}$, $C_{4-10}$, $C_{6-14}$, $C_{6-12}$, $C_{6-10}$, $C_{8-14}$, $C_{8-12}$, or preferably $C_{8-10}$fluoroalkyl. In preferred embodiments, the fluoroalkyl substituting the alkyl in $R^{10}$ is perfluoroalkyl.

In embodiments, the alkyl is $R^{21}$, $R^{22}$ and $R^{23}$ is $C_{4-12}$, $C_{6-12}$, $C_{8-12}$, $C_{4-10}$, $C_{6-10}$, $C_{8-10}$, $C_{4-8}$, $C_{6-8}$, or $C_8$alkyl.

In embodiments, each of the alkyl group of the alkyl-O-alkyl in $R^{21}$, $R^{22}$ and $R^{23}$ is $C_{4-12}$, $C_{6-12}$, $C_{8-12}$, $C_{4-10}$, $C_{6-10}$, $C_{8-10}$, $C_{4-8}$, $C_{6-8}$, or $C_8$alkyl.

In embodiments, the aryl in $R^{21}$, $R^{22}$ and $R^{23}$ is phenyl.

The optional substituent(s) of the aryl in $R^{21}$, $R^{22}$ and $R^{23}$ is(are) fluoride atoms, alkyl or alkoxy. In embodiments, the alkyl/alkoxy optionally substituting the aryl in $R^{21}$, $R^{22}$ and $R^{23}$ is a $C_{1-6}$, $C_{1-5}$, $C_{1-4}$, $C_{1-3}$, $C_{2-6}$, $C_{2-5}$, $C_{2-4}$, or $C_{2-3}$ alkyl/alkoxy. In preferred embodiments, the aryl is unsubstituted.

In embodiments, $R^{10}$ correspond to the $R^{10}$ group in the "second silyl compounds" shown in Table 1 below.

In more preferred embodiments, $R^{10}$ is 1H,1H,2H,2H-perfluorooctyl [i.e. $-CH_2-CH_2-(CF_2)_5-CF_3$], 1H,1H,2H,2H-perfluorodecyl [i.e. $-CH_2-CH_2-(CF_2)_7-CF_3$], 3,3,3-trifluoropropyl [i.e. $-CH_2-CH_2-CF_3$], pentafluorophenyl (i.e. perfluorophenyl;

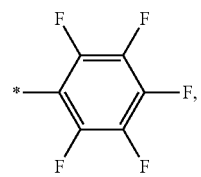 [SMILES: *c1c(F)c(F)c(F)c(F)c1F]

the star indicating the point of attachment), octyl, or 3-glycidyloxypropyl

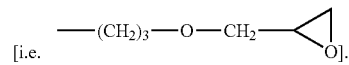

[i.e. $-(CH_2)_3-O-CH_2-$ ].

In preferred embodiments, $R_{10}$ is unsubstituted alkyl or alkyl substituted with fluoroalkyl, preferably perfluoroalkyl. In more preferred embodiments, $R^{10}$ is 1H,1H,2H,2H-perfluorooctyl, 1H,1H,2H,2H-perfluorodecyl, 3,3,3-trifluoropropyl, or octyl. In most preferred embodiments, $R^{10}$ is 1H,1H,2H,2H-perfluorooctyl, 1H,1H,2H,2H-perfluorodecyl, or octyl.

In most preferred embodiments, the oligomer is:

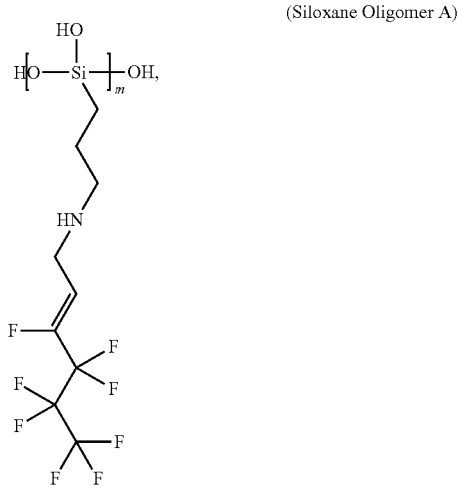

(Siloxane Oligomer A)

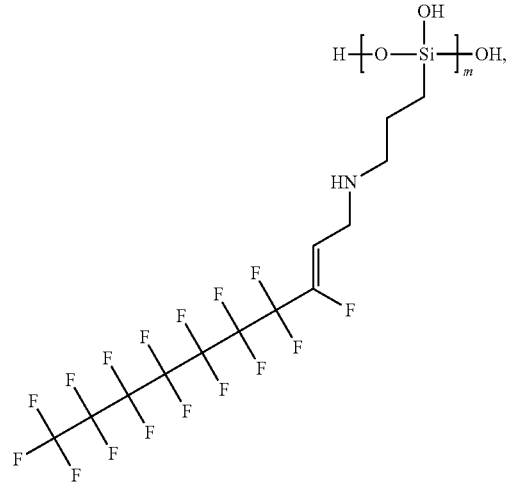

(Siloxane Oligomer B)

-continued
(Siloxane Oligomer C)
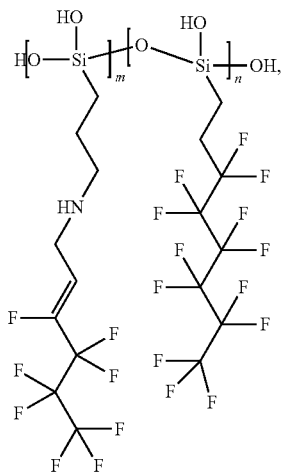
(Siloxane Oligomer D)
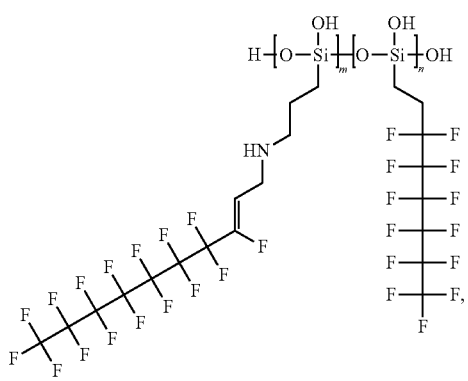
(Siloxane Oligomer E)
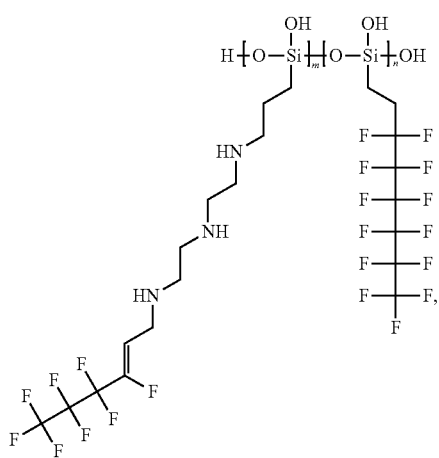
-continued
(Siloxane Oligomer F)
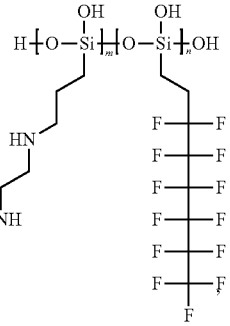
(Siloxane Oligomer G)
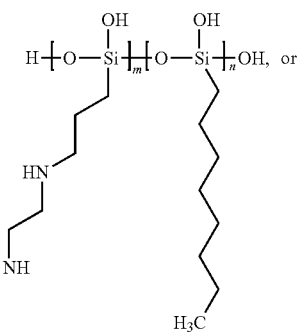
(Siloxane Oligomer H)
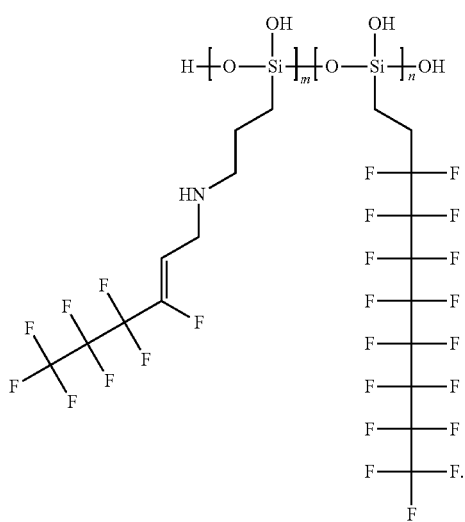

In more preferred embodiments, the siloxane oligomer is Siloxane Oligomer A, B, C, D, E, G, or H (as defined above).

In embodiments, the siloxane oligomers of the invention are water-soluble. Herein, "water-soluble" means that the siloxane oligomers can be dissolved in water or in an aqueous solution at least up to a concentration at which they are active for their intended use (e.g. for changing the hydrophobicity or lipophilicity of a surface or for self-propulsion on a surface). As will be seen in the Examples below, this minimum effective concentration can be quite low (e.g. about 0.1%). In embodiments where a water-soluble siloxane oligomer is desired, care should be taken to avoid combining together repeat units with overly long hydrophobic chains, which might compromise water solubility.

Advantages and Uses of the Siloxane Oligomers of the Invention

When applied to a surface of a solid substrate, the siloxane oligomers of the invention render the surface more hydrophobic and/or more lipophobic, preferably both more hydrophobic and more lipophobic, than it was before application. The siloxane oligomer of the invention form, when applied, a hydrophobic and/or lipophobic coating on the surface.

This effect has been observed on a variety of substrates, both porous and non-porous, including wood, metal, glass, fabric and concrete surfaces, preferably glass, fabric or concrete, more preferably glass. Preferably, the surface is a glass surface as results on glass substrates are particularly interesting—see the Examples below. Nonetheless, it should be noted that the results on the other surface are also good. This opens a wide framework of applications.

This effect has been observed at concentrations as low as 0.1% in water—see the examples below.

This effect can be temporary and longer lasting (and even permanent) depending on the nature of the siloxane oligomers and solid substrate. In some cases, the siloxane oligomers will wash away, while in other cases, they will remain attached to the surface of the substrate.

The structure of the monomers used to produce the siloxane oligomers can be tailored according to the desired hydrophobicity and lipophobicity for a given substrate and to alter the surface in additional ways. Examples of desirable surface alterations include conferring antibacterial properties, anti-scratch properties. The concentration of the siloxane oligomers will also affect the resulting hydrophobicity and lipophobicity.

In embodiments, the siloxane oligomers of the invention are water-soluble (contrary to most commercially available conventional surface treatments). The oligomer of the invention nevertheless exhibit performances on par with of better than these conventional surface treatments.

As such, there is provided herein a method of increasing the hydrophobicity and/or the lipophobicity of a surface of a solid substrate, including wood, metal, glass, fabric and concrete surfaces, preferably glass, fabric or concrete, more preferably glass, the method comprising contacting the above siloxane oligomer with the surface. Optionally, the method further comprises the step of rinsing the surface. Optionally, the method further comprises the step of drying the surface.

There is also provided a solid substrate, including wood, metal, glass, fabric and concrete surfaces, preferably glass, fabric or concrete, more preferably glass, having deposited on a surface thereon a coating of the above siloxane oligomer. The surface of the solid substrate with the siloxane oligomer being more hydrophobic and/or more lipophobic than an equivalent surface without the siloxane oligomer.

Furthermore, when in (preferably aqueous) solution, the siloxane oligomers of the invention can be self-propelling when deposited on a solid surface, preferably glass—see the Examples below. This effect has been observed on horizontal surfaces and inclined surfaces, on which the solution moved against gravity force. This opens a variety of applications in, for example, liquid transportation, soft-printing, drug delivery, and microfluidics.

This effect has also been observed at concentrations as low as 0.1% in water—see the examples below.

Therefore, there is provided a (preferably aqueous) solution of the above siloxane oligomer; this solution being self-propelling when put in contact with a solid surface, preferably a glass surface.

There is also provided a method of transporting a fluid, the method comprising the step of placing a solution of the above siloxane oligomer (as said fluid to be transported), in contact with a solid surface, preferably a glass surface, and allowing the solution to self-propel on the surface. It should be noted that, in the areas exposed to the solution, i.e. on which the solution has travelled by self-propulsion, this will change the surface tension of the surface.

Synthesis of the Siloxane Oligomers

The siloxane oligomers can be manufactured from a first silyl compound, alone or combined with a second silyl compound.

The first silyl compound is of formula:

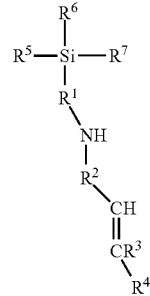

wherein:
$R^1$, $R^2$, $R^3$ and $R^4$ are as defined above, including preferred embodiments thereof, and
$R^5$, $R^6$, and $R^7$ are independently chloro or alkoxy.

In embodiments, the alkoxy in $R^5$, $R^6$, and $R^7$ is (independently) $C_{1-5}$, $C_{1-4}$, $C_{1-3}$, or $C_{1-2}$ alkoxy.

In preferred embodiments, $R^5$, $R^6$, and $R^7$ are the same. In most preferred embodiments, $R^5$, $R^6$, and $R^7$ are alkoxy. In embodiments, the alkoxy is methoxy or ethoxy.

In most preferred embodiments, the first silyl compound is:

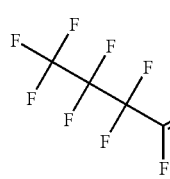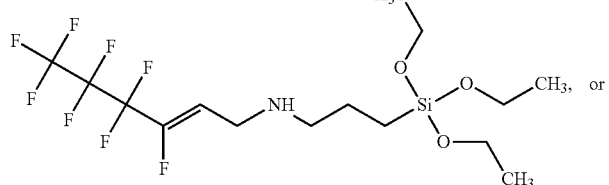

-continued

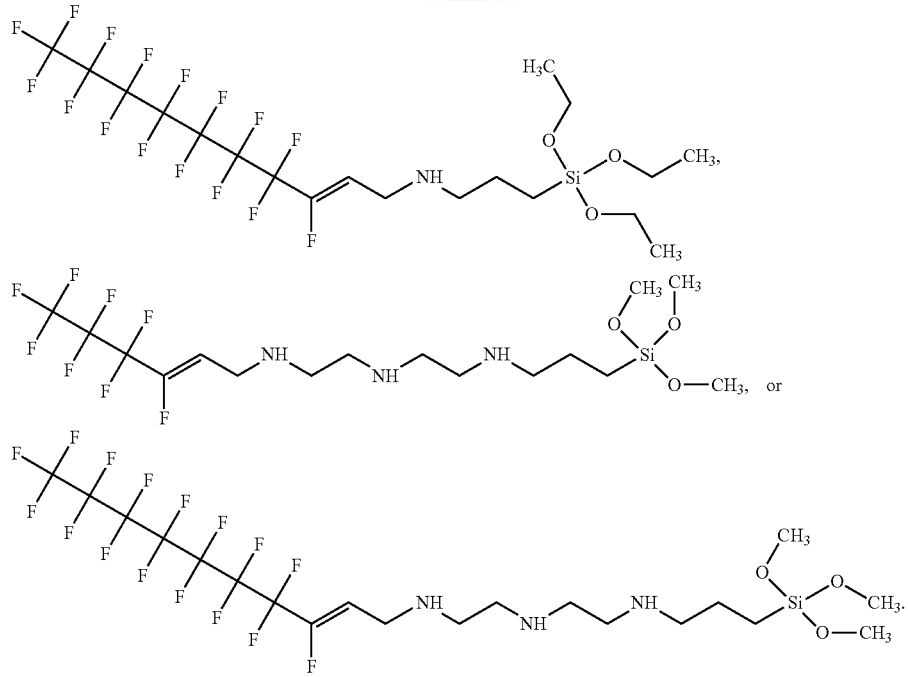

The second silyl compound is of formula:

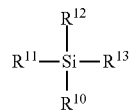

wherein:
$R^{10}$ is as defined above, including preferred embodiments thereof, and
$R^{11}$, $R^{12}$, and $R^{13}$ are independently chloro or alkoxy.

In embodiments, the alkoxy in $R^{11}$, $R^{12}$, and $R^{13}$ is (independently) $C_{1-5}$, $C_{1-4}$, $C_{1-3}$, or $C_{1-2}$ alkoxy.

In preferred embodiments, $R^{11}$, $R^{12}$, and $R^{13}$ are the same. In most preferred embodiments, $R^{11}$, $R^{12}$, and $R^{13}$ are alkoxy. In embodiments, the alkoxy is methoxy or ethoxy, preferably ethoxy.

In preferred embodiments, the second silyl compound is a commercially available second silyl compound.

Non-limiting examples of the second silyl compound include:

TABLE 1

| Second Silyl Compound | CAS Number | Structure |
|---|---|---|
| 1H,1H,2H,2H-perfluorooctyltriethoxysilane | 51851-37-7 | 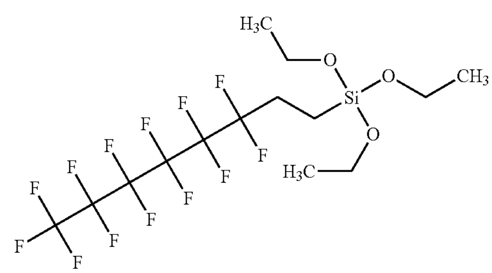 [SMILES: CCO[Si](CCC(F)(F)C(F)(F)C(F)(F)C(F)(F)C(F)(F)C(F)(F)F)(OCC)OCC] |
| 1H,1H,2H,2H-perfluorooctyltrimethoxysilane | 85857-16-5 | 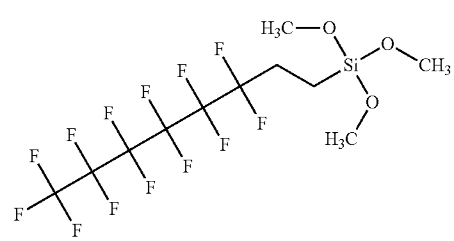 [SMILES: CO[Si](CCC(F)(F)C(F)(F)C(F)(F)C(F)(F)C(F)(F)C(F)(F)F)(OC)OC] |

TABLE 1-continued

| Second Silyl Compound | CAS Number | Structure |
|---|---|---|
| 1H1H 2H 2H-perfluorooctyltrichlorosilane | 78560-45-9 | 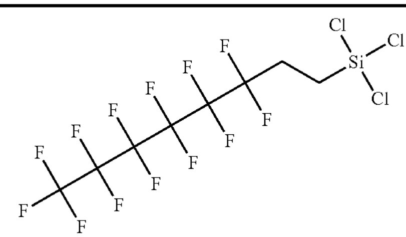 |
| 1H,1H,2H,2H-Perfluorodecyltriethoxysilane | 101947-16-4 | 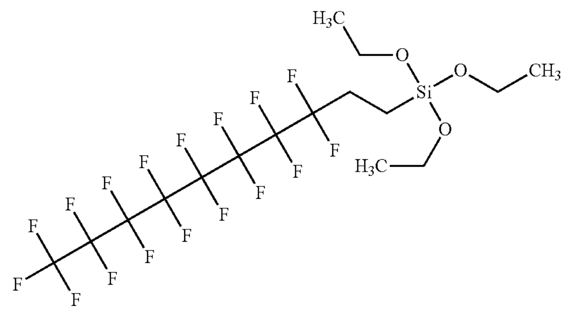 [SMILES: CCO[Si](CCC(F)(F)C(F)(F)C(F)(F)C(F)(F)C(F)(F)C(F)(F)C(F)(F)C(F)(F)F)(OCC)OCC] |
| 1H,1H,2H,2H-Perfluorodecyltrimethoxysilane | | 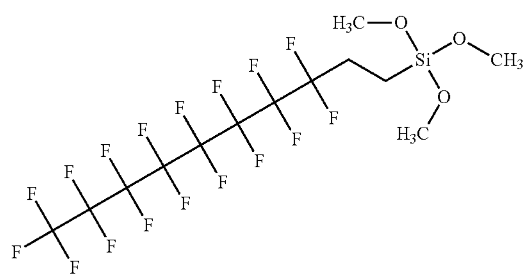 [SMILES: CO[Si](CCC(F)(F)C(F)(F)C(F)(F)C(F)(F)C(F)(F)C(F)(F)C(F)(F)C(F)(F)F)(OC)OC] |
| 1H,1H,2H,2H-Perfluorodecyltrichlorosilane | 78560-44-8 | 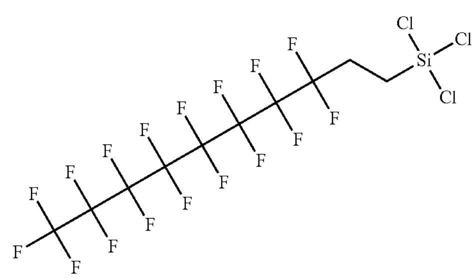 [SMILES: FC(F)(F)C(F)(F)C(F)(F)C(F)(F)C(F)(F)C(F)(F)C(F)(F)C(F)(F)CC[Si](Cl)(Cl)Cl] |
| Trimethoxy(3,3,3-trifluoropropyl)silane | 429-60-7 | 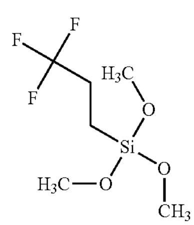 |
| Triethoxy(3,3,3-trifluoropropyl)silane | | 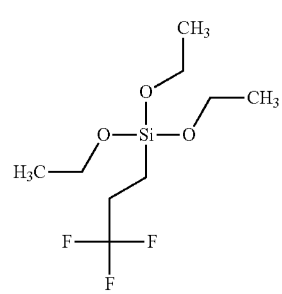 [SMILES: CCO[Si](CCC(F)(F)F)(OCC)OCC] |

TABLE 1-continued

| Second Silyl Compound | CAS Number | Structure |
|---|---|---|
| Trichloro(3,3,3-trifluoropropyl)silane | 592-09-6 | 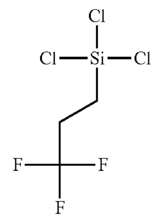 |
| (Pentafluorophenyl)triethoxysilane | 20083-34-5 | 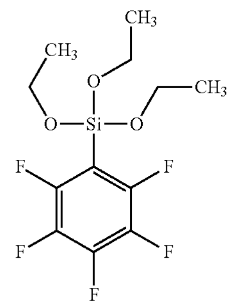 [SMILES: CCO[Si](OCC)(OCC)c1c(F)c(F)c(F)c(F)c1F] |
| Pentafluorophenyl)trimethoxysilane | | 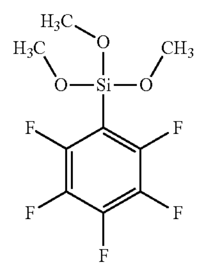 [SMILES: CO[Si](OC)(OC)c1c(F)c(F)c(F)c(F)c1F] |
| Pentafluorophenyl)trichlorosilane | | 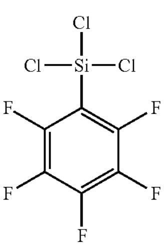 |
| Triethoxy(octyl)silane | 2943-75-1 | 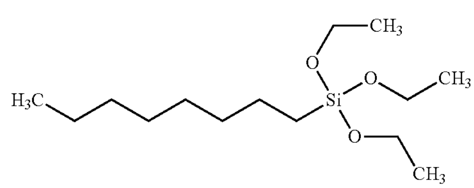 [SMILES: CCCCCCCC[Si](OCC)(OCC)OCC] |
| Trimethoxy(octyl)silane | 3069-40-7 | 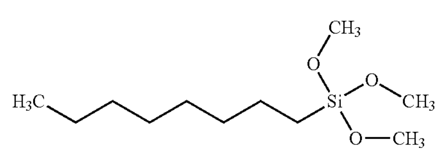 |
| Trichloro(octyl)silane | 5283-66-9 | 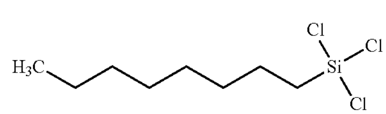 |

TABLE 1-continued

| Second Silyl Compound | CAS Number | Structure |
| --- | --- | --- |
| Diethoxy(3-glycidyloxypropyl)methylsilane | 2897-60-1 | 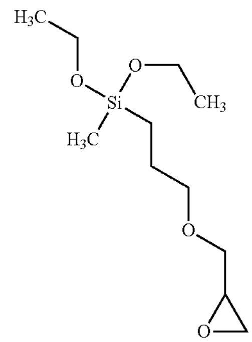 [SMILES: CCO[Si](C)(CCCOCC1CO1)OCC] |
| 2-hydroxy-4-(3-triethoxysilylpropoxy)diphenylketone (and the corresponding compound in which the ethoxy groups are replaced by methoxy groups) | 79876-59-8 | 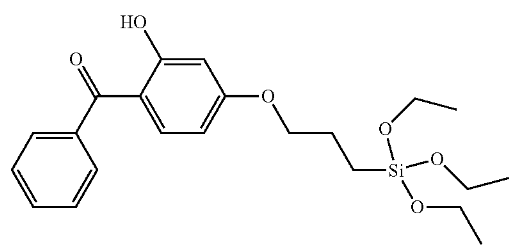 [SMILES: CCO[Si](CCCOc1ccc(C(=O)c2ccccc2)c(O)c1)(OCC)OCC] |
| Dimethoxy(3-glycidyloxypropyl)methylsilane | | 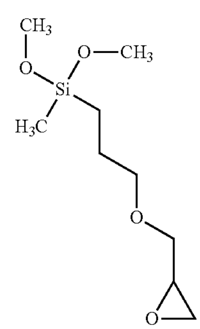 |
| Dichloro(3-glycidyloxypropyl)methylsilane | | 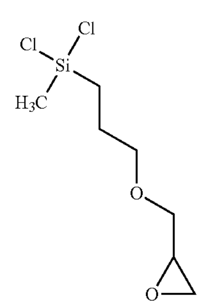 |

More specifically, the siloxane oligomers of the invention can be synthesized by hydrolysis/oligomerization of the first silyl compound alone or with a second silyl compound. A specific example of this reaction (in which the first silyl compound is used alone) is:

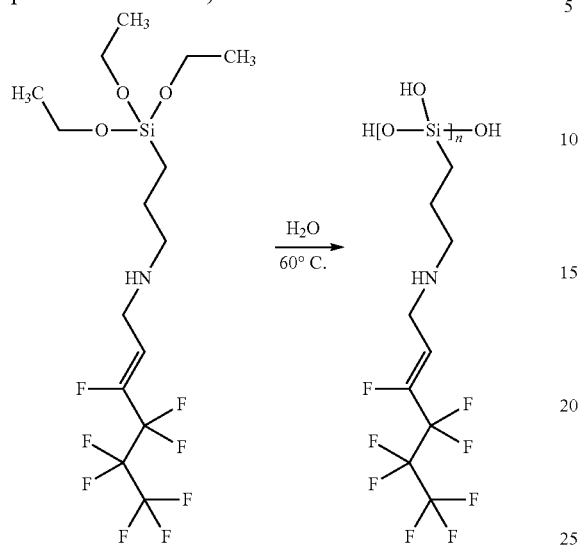

When a second silyl compound is used, it is simply added to the reaction mixture and reacts similarly to the first silyl compounds of the invention. A specific example of this reaction is:

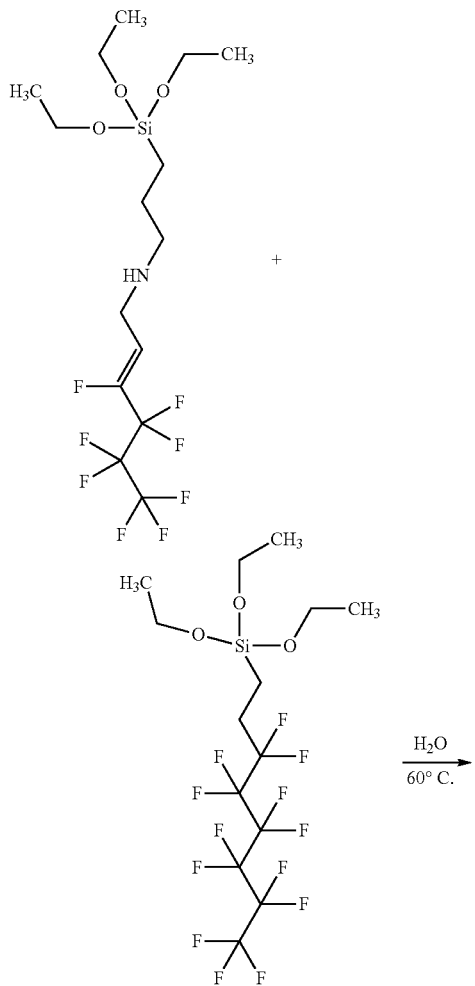

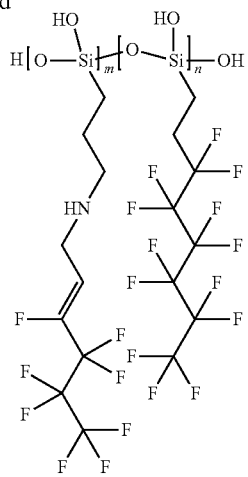

The molar ratio of the first silyl compound of the reaction to the second silyl compound can vary between 0.01:1 and 100:1. In preferred embodiments, the ratio is between about 1:1 and about 100:1, preferably between about 10:1 and about 100:1.

The typical reaction temperature is between about 25 and about 60° C., preferably at about 60° C.

The amount of water added to reaction could be between 0.1 and 3 molar equivalents of the total hydrolysable functions present in the reaction mixture, preferably at least about 1 equivalent.

The reaction time typically varies between about 3 h and about 24 h, preferably the reaction time is about 4 h.

The degree of oligomerization of the final product will vary significantly and yield oligomer chains of different lengths. Thus, the oligomer is obtained as a mixture of oligomers with m is 1 or greater and n is 0 if a second silyl compound is not used or 1 or greater if a second silyl compound is used.

Synthesis of the First Silyl Compounds

The first silyl compounds, used in the manufacture of the siloxane oligomers of the invention, can be prepared by direct reaction of an alkene with an amino alkyl silane using a basic catalyst. A specific example of this reaction is:

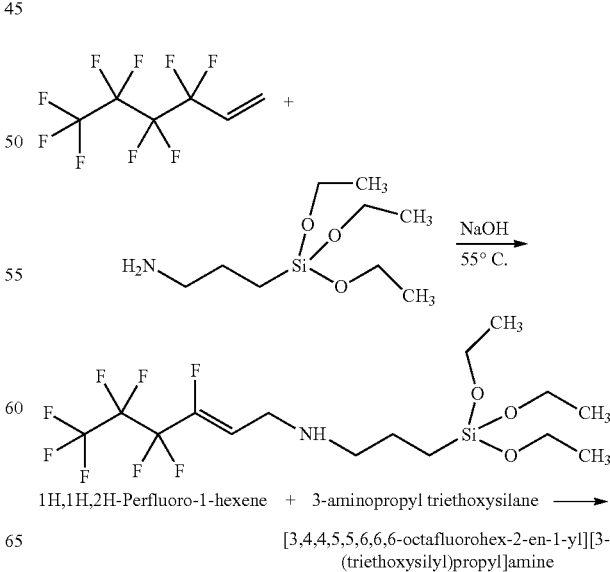

1H,1H,2H-Perfluoro-1-hexene + 3-aminopropyl triethoxysilane ⟶

[3,4,4,5,5,6,6,6-octafluorohex-2-en-1-yl][3-(triethoxysilyl)propyl]amine

Non-limiting examples of suitable alkenes include:

TABLE 2

| Alkene | CAS Number | Structure |
|---|---|---|
| 1H,1H,2H-Perfluoro-1-hexene | 19430-93-4 | $CF_3(CF_2)_3CH{=}CH_2$ |
| 1H,1H,2H-Perfluoro-1-octene | 25291-17-2 | $CF_3(CF_2)_5CH{=}CH_2$ |
| 1H,1H,2H-Perfluoro-1-decene | 21652-58-4 | $CF_3(CF_2)_7CH{=}CH_2$ |
| 1-hexene | 592-41-6 | $CH_3(CH_2)_3CH{=}CH_2$ |

TABLE 2-continued

| Alkene | CAS Number | Structure |
|---|---|---|
| 1-octene | 111-66-0 | $CH_3(CH_2)_5CH{=}CH_2$ |
| 1-Decene | 872-05-09 | $CH_3(CH_2)_7CH{=}CH_2$ |

Non-limiting examples of suitable amino alkyl silane include:

TABLE 3

| Amino alkyl silane | CAS Number | Structure |
|---|---|---|
| 3-aminopropyl triethoxysilane | 919-30-2 | 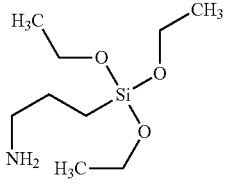 |
| 3-aminopropyl trimethoxysilane | 13822-56-5 | 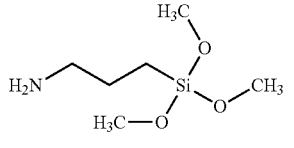 |
| 3-aminopropyl trichlorosilane | 63823-23-4 | 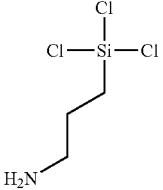 |
| 4-aminobutyltriethoxysilane | 3069-30-5 | 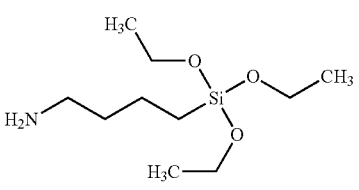 |
| 4-aminobutyltrimethoxysilane | 15005-59-1 | 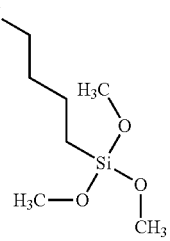 |
| 4-aminobutyltrichlorosilane | | 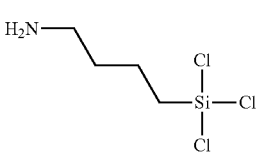 |
| N-[3-(trimethoxysilyl)propyl]ethylenediamine | 1760-24-3 | 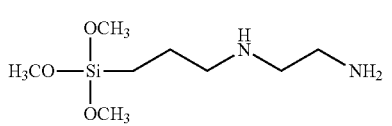 |

TABLE 3-continued

| Amino alkyl silane | CAS Number | Structure |
|---|---|---|
| N-[3-(triethoxysilyl)propyl]ethylenediamine | 5089-72-5 | |
| N-[3-(trichlorosilyl)propyl]ethylenediamine | | |
| $N^1$-(3-trimethoxysilylpropyl)diethylenetriamine | 35141-30-1 | |
| $N^1$-(3-triethoxysilylpropyl)diethylenetriamine | | |
| $N^1$-(3-trichlorosilylpropyl)diethylenetriamine | | |

Non-limiting examples of suitable catalysts include sodium hydroxide, sodium alkoxides (such as sodium methoxide and sodium ethoxide), lithium hydroxide, potassium hydroxide or 4-dimethylaminpyridine (CAS number: 1122-58-3), preferably sodium hydroxide.

The typical reaction temperature is between 30 and 70° C., preferably 55° C.

The molar ratio of the reactants amino alkyl silane:alkene typically varies between 0.5:1 and 1:2. Preferably, this ratio is about 1:1.

The reaction time typically varies between about 4 h and about 24 h, preferably the reaction time is 20 h.

The catalyst: reactants molar ratio, the reactants being the amino alkyl silane and the alkene, typically varies between 0.001:1 and 0.1:1. Preferably, this ratio is about 0.1:1.

The reaction can be carried out without a solvent as the reactants are liquid. However, if desired an aprotic solvent, such as acetonitrile, can be used.

At the end of the reaction, an acid is used to neutralize the amine group and the catalyst. This can be done after producing the silyl compound or after using the silyl compound to produce the siloxane oligomer. In both case, the acid can be for example acetic acid, formic acid, or methanesulfonic acid.

Definitions

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

Similarly, herein a general chemical structure, with various substituents ($R_1$, $R_2$, etc.) and various radicals (alkyl, halogen atom, etc.) enumerated for these substituents is intended to serve as a shorthand method of referring individually to each and every molecule obtained by the combination of any of the radicals for any of the substituents. Each individual molecule is incorporated into the specification as if it were individually recited herein. Further, all subsets of molecules within the general chemical structures are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

Herein, the term "about" has its ordinary meaning. In embodiments, it may mean plus or minus 10% or plus or minus 5% of the numerical value qualified.

Unless otherwise defined, all technical and scientific terms used herein have the same meaning as commonly understood by one of ordinary skill in the art to which this invention belongs.

Herein, the terms "alkyl" "alkylene" and their derivatives (such as alkoxy, fluoroalkyl etc.) have their ordinary meaning in the art. For more certainty, herein:

TABLE 4

| Term | Definition |
| --- | --- |
| alkyl | monovalent saturated aliphatic hydrocarbon radical of general formula —$C_nH_{2n+1}$ |
| alkylene | bivalent saturated aliphatic hydrocarbon radical of general formula —$C_nH_{2n}$— (also called alkanediyl) |
| alkoxy | monovalent radical of formula —O-alkyl |
| fluoroalkyl | alkyl radical substituted with one or more fluoro atom, up to and including perfluoroalkyls in which the alkyl is completely substituted with fluoro atoms |

It is to be noted that, unless otherwise specified, the hydrocarbon chains of the above groups can be linear or branched, preferably they are linear. Further, unless otherwise specified, these groups can contain between 1 and 18 carbon atoms, more specifically between 1 and 12 carbon atoms, between 1 and 6 carbon atoms, between 1 and 3 carbon atoms, or contain 1 or 2, preferably 1 carbon atom, or preferably 2 carbon atoms.

Herein, the terms "cycloalkyl" and "aryl" have their ordinary meaning in the art. For more certainty, herein:

TABLE 5

| Term | Definition |
| --- | --- |
| aryl | monovalent aromatic hydrocarbon radical presenting a delocalized conjugated Π system, most commonly an arrangement of alternating double and single bonds, between carbon atoms arranged in one or more rings, wherein the rings can be fused (i.e. share two ring atoms), for example: naphthalene: or linked together through a covalent bond, for example: biphenyl: or linked together through a radical that allow continuation of the delocalized conjugated Π system between the rings (e.g. —C(=O)—, —NRR—), for example: benzophenone: |
| aryloxy | monovalent radical of formula —O-aryl |
| fluoroaryl | aryl radical substituted with one or more fluoro atoms, up to and including perfluoroaryls in which the aryl is completely substituted with fluoro atoms |

It is to be noted that, unless otherwise specified, each ring of the above groups can comprise between 4 and 8, preferably 5 or 6 ring atoms. Also, unless otherwise specified, the above groups preferably comprise 1 or 2 rings, more preferably one ring, which is preferably phenyl ($C_6$).

Herein, the term "interrupted" as in "alkylene optionally interrupted by one or more . . . group" means that at least one of said group is inserted between two adjacent carbon atoms of the alkylene group.

Herein, a radical "substituted with group X" means that one or more hydrogen atoms of the radical is replaced with said group X. When a radical is end-substituted with group X, the hydrogen atom that is replaced with a group X located at the end of the radical opposite its point of attachment. For example, a butyl end-substituted with fluoroalkyl is: *—$CH_2$—$CH_2$—$CH_2$—$^{\#CH}{}_2$-fluoroalkyl, wherein for clarity, a * represents the point of attachment and a # identifies the carbon atom at the end of the radical opposite the point of attachment.

When a radical is persubstituted (with group X), for example, perfluoroalkyls and perfluoroaryls, the radical is completely substituted. In other words, all the hydrogen atoms of the radical are each replaced with group X.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

The present invention is illustrated in further details by the following non-limiting examples.

Example 1

Synthesis of Silyl Compounds

Sylyl Compound 1

Silyl Compound 1, [3,4,4,5,5,6,6,6-octafluorohex-2-en-1-yl] [3-(triethoxysilyl)propyl]amine, was synthesized according to the following scheme:

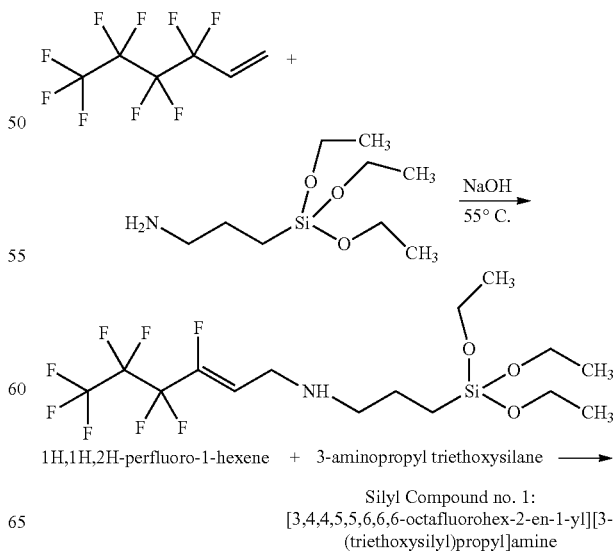

1H,1H,2H-perfluoro-1-hexene + 3-aminopropyl triethoxysilane ⟶

Silyl Compound no. 1:
[3,4,4,5,5,6,6,6-octafluorohex-2-en-1-yl][3-(triethoxysilyl)propyl]amine 395.0 gr of 1H,1H,2H perfluorol-hexene, 357.0 g of 3-aminopropyl triethoxysilane and 11.3 g sodium hydroxide are added to a reactor. The temperature was increased to 55° C. and the mixture was stirred for 17 hours. After 17 h, the reactor was left to cool down to ambient temperature. A turbid yellow mixture was obtained.

Figure 2:
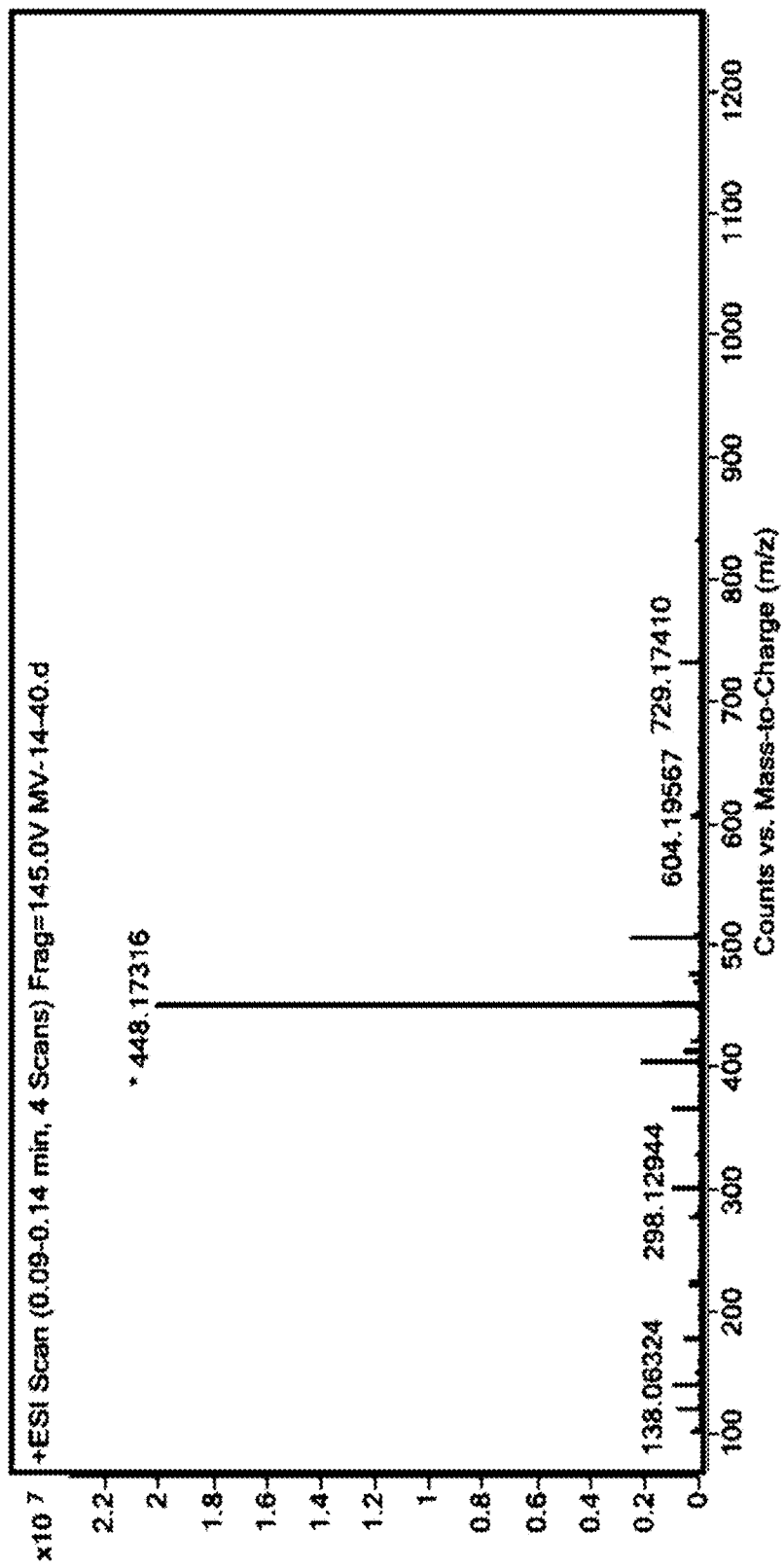
FIG. 2 shows the mass spectrum of [3,4,4,5,5,6,6,6-octafluorohex-2-en-1-yl] [3-(triethoxysilyl)propyl]amine.

The product was characterized by mass spectrometry. The predicted molecular weight of Silyl Compound no. 1, based on above reaction, is 447.44 g/mol ($C_{15}H_{25}F_8Si_1N_1O_3$). FIG. 2 shows the mass spectrum (+MI) of the reaction product.

Figure 3A:
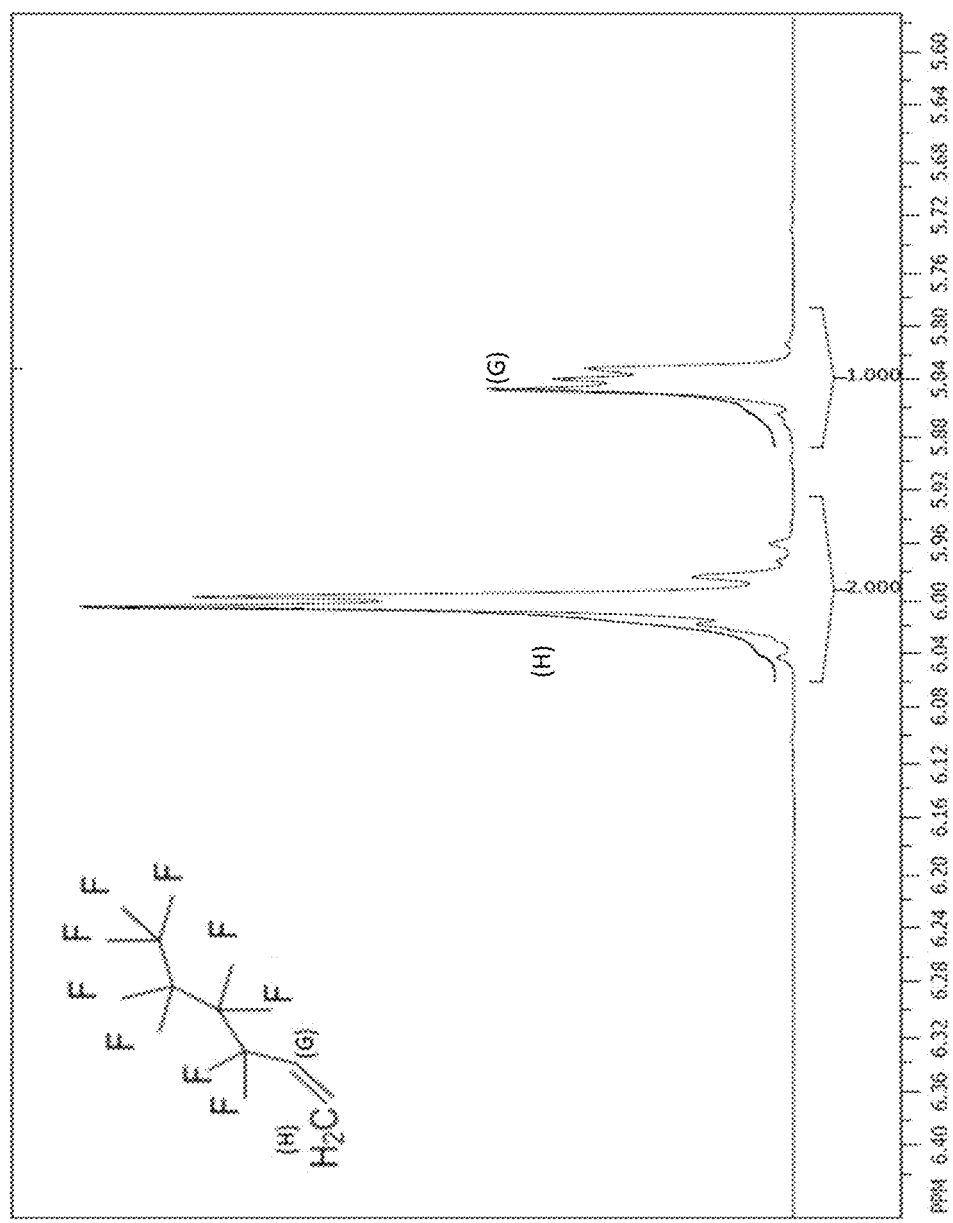
FIG. 3A) shows the $^1$H NMR spectra of 1H,1H,2H-Perfluoro-1-hexene.
Figure 3B:
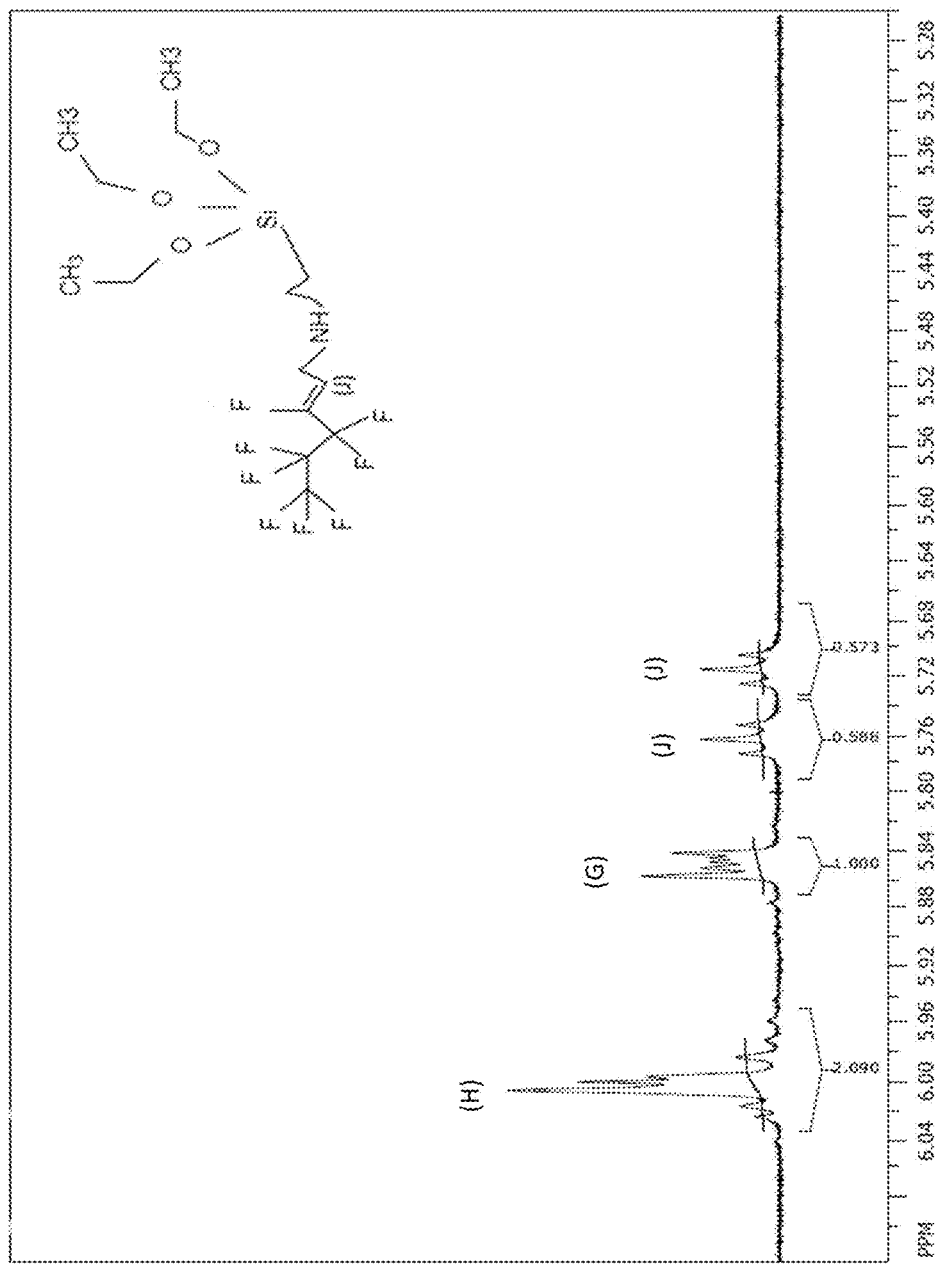
FIG. 3B) shows the $^1$H NMR spectra of [3,4,4,5,5,6,6,6-octafluorohex-2-en-1-yl] [3-(triethoxysilyl)propyl]amine.

FIGS. 3A) and B) allow comparing the $^1$H NMR spectra of one of the starting materials (1H,1H,2H-Perfluoro-1-hexene) and the synthesized product in the same spectral region. The spectrum of the synthesized product exhibits two triplets (labelled J) indicating the presence of the two different isomers of Silyl Compound no. 1. The splitting is caused by two protons of the neighbor $CH_2$. Also, some of the starting material (1H,1H,2H-perfluoro-1-hexene) remains in the product.

Figure 4A:
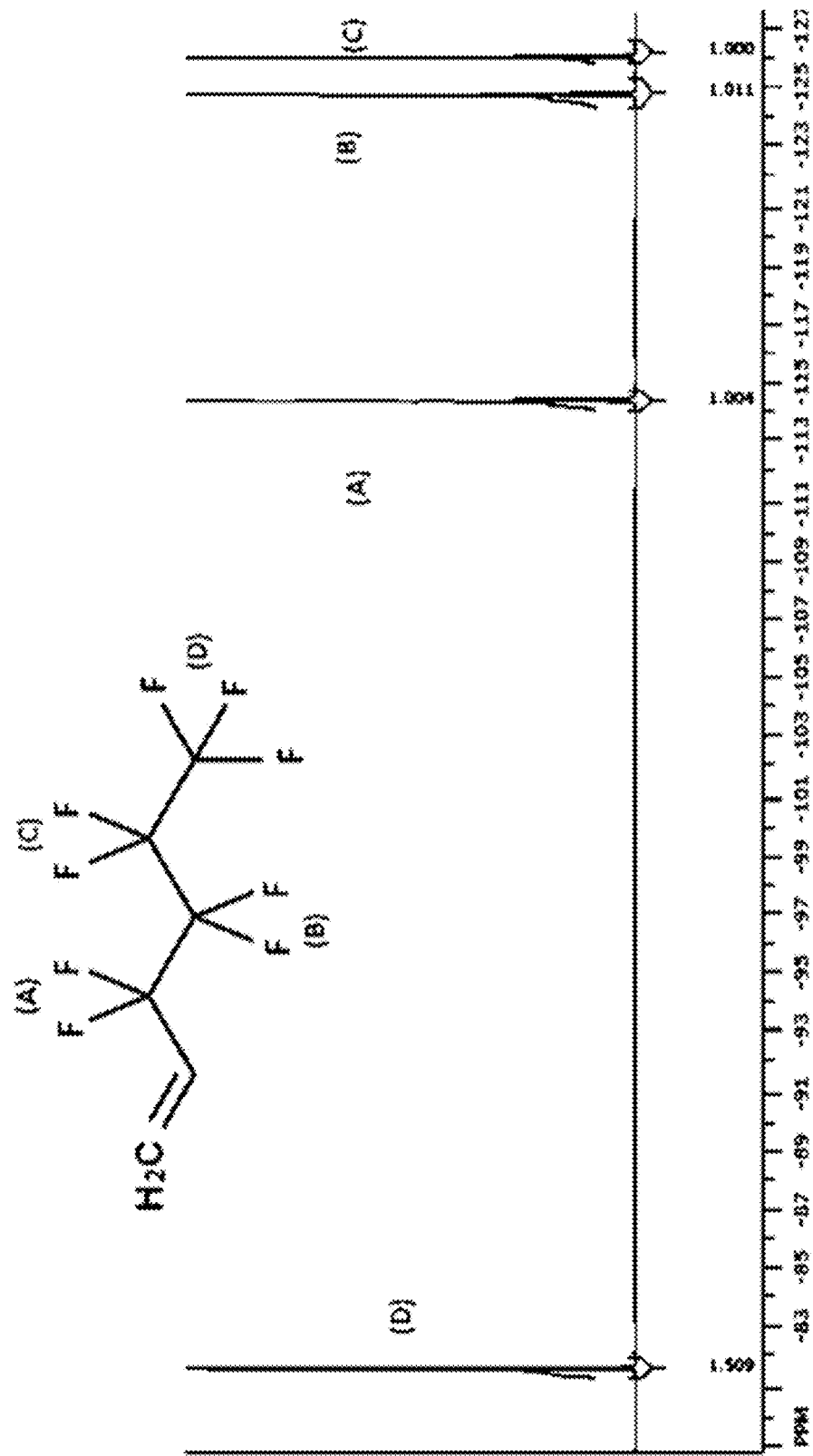
FIG. 4A) shows the F NMR spectra of 1H,1H,2H-Perfluoro-1-hexene.
Figure 4B:
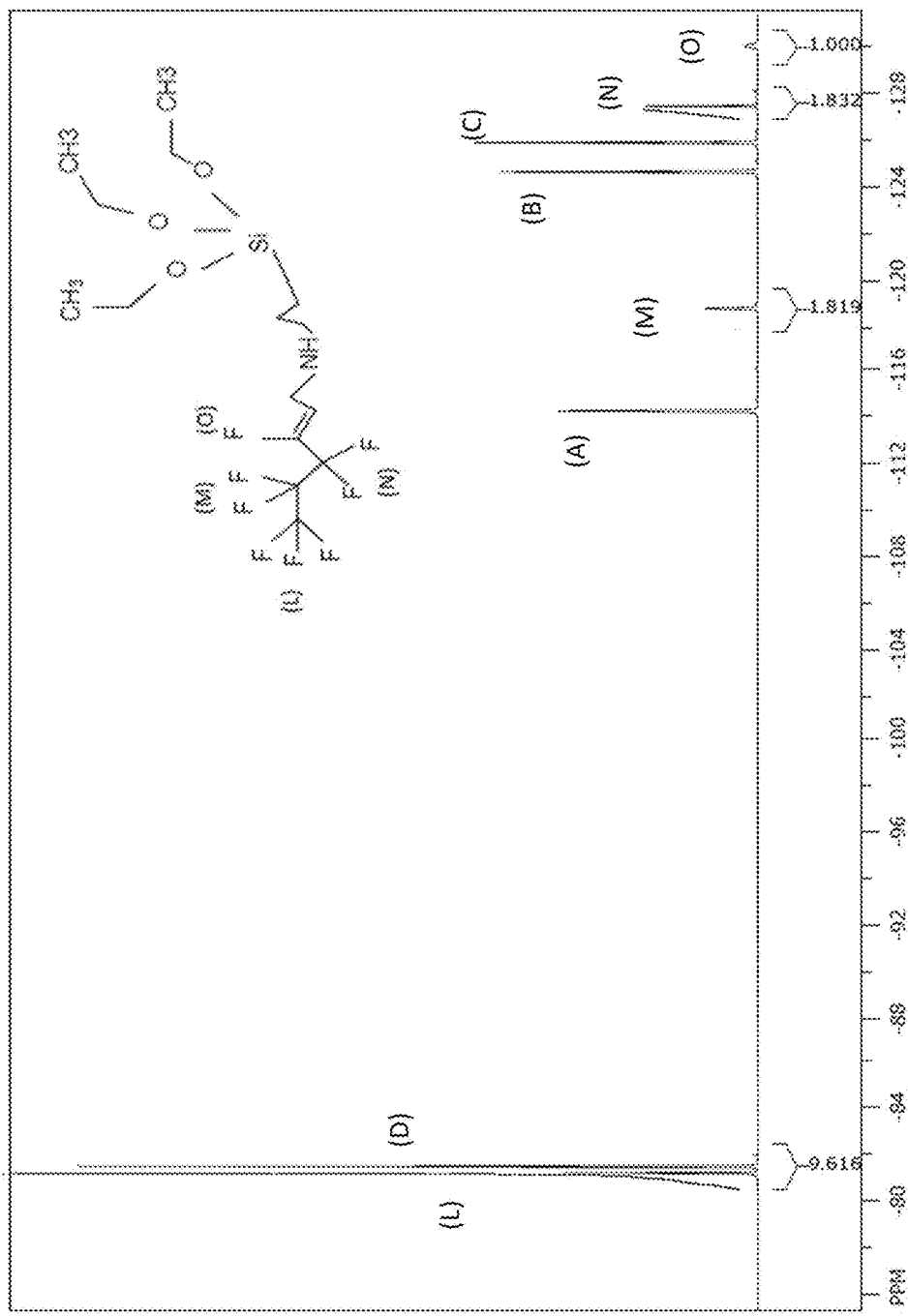
FIG. 4B) shows the F NMR spectra of [3,4,4,5,5,6,6,6-octafluorohex-2-en-1-yl] [3-(triethoxysilyl)propyl]amine.

FIGS. 4A) and B) allow comparing the F NMR spectra of one of the starting materials (1H,1H,2H-Perfluoro-1-hexene) and the synthesized product in the same spectral region. The spectrum of the 1H,1H,2H-perfluoro-1-hexene is presented in FIG. 4A) with peak assignments and integral values for each peak. FIG. 4B) shows the F NMR spectrum of the synthesized product. The integrals of the newly formed peaks are in accord with the above chemical structure. The peaks of the raw material are also present in the final product.

Silyl Compounds $1^I$ to $1^V$

Silyl Compound 1 was also prepared using other bases as catalysts and, in one case, a solvent. More specifically:

Silyl Compound $1^I$ was prepared in a manner similar to Silyl Compound 1, except that LiOH was used instead of NaOH.

Silyl Compound $1^{II}$ was prepared in a manner similar to Silyl Compound 1, except that KOH was used instead of NaOH.

Silyl Compound $1^{III}$ was prepared in a manner similar to Silyl Compound 1, except that $NaOCH_3$ was used instead of NaOH.

Silyl Compound $1^{IV}$ was prepared in a manner similar to Silyl Compound 1, except that $NaOCH_2CH_3$ was used instead of NaOH.

Silyl Compound $1^V$ was prepared in a manner similar to Silyl Compound 1, except that the reaction took place in an protic solvent: acetonitrile.

Silyl Compound 2

Silyl Compound 2, [3,4,4,5,5,6,6,7,7,8,8,9,9,10,10,10-hexadecafluorodec-2-en-1-yl] [3-(triethoxysilyl)propyl] amine, was prepared in a manner similar to Silyl Compound 1, except that 1H,1H,2H-perfluoro-1-decene was used instead of 1H,1H,2H-perfluoro-1-hexene.

Silyl Compound no. 2

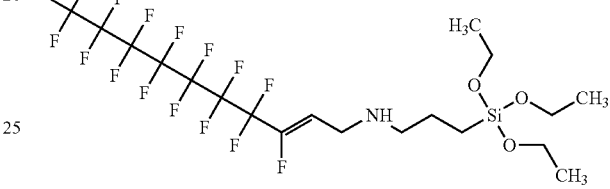

Silyl Compound 3

Silyl Compound 3 was prepared in a manner similar to Silyl Compound 1, except that $N^1$-(3-trimethoxysilylpropyl)diethylenetriamine was used instead of 3-aminopropyl triethoxysilane.

Silyl Compound 3

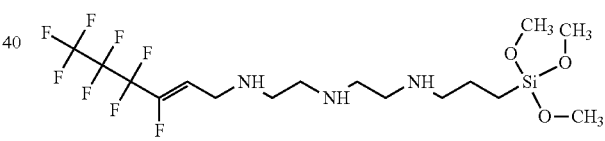

Silyl Compound 4

Silyl Compound 4 was prepared in a manner similar to Silyl Compound 1, except that:

$N^1$-(3-trimethoxysilylpropyl)diethylenetriamine was used instead of 3-aminopropyl triethoxysilane, and 1H,1H,2H-perfluoro-1-decene was used instead of 1H,1H,2H-perfluoro-1-hexene.

Silyl Compound 4

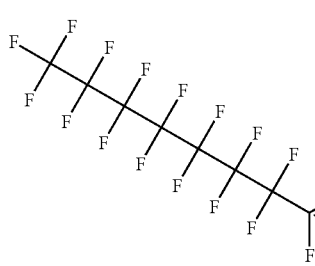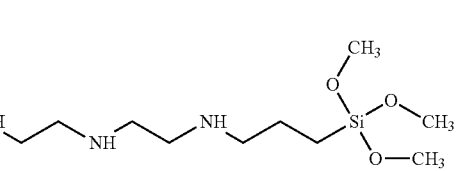

Example 2

Synthesis of Siloxane Oligomers

Siloxane Oligomer A

Siloxane Oligomer A was synthesized according to the following reaction scheme:

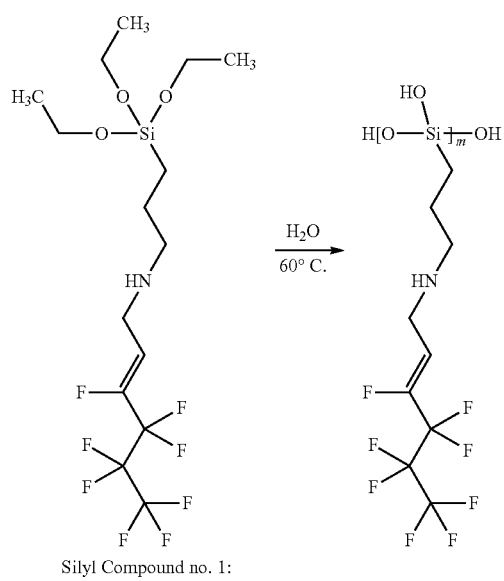

Silyl Compound no. 1:
[3,4,4,5,5,6,6,6-octafluorohex-2-en-1-yl]
[3-(triethoxysilyl)propyl]amine (of Example 1)

Siloxane Oligomer A
1H,1H,2H,2H-perfluorooctyl-triethoxysilane 763.3 g of Silyl Compound no. 1 of Example 1 and 58.15 g deionized were added to a reactor, the hydrolysis reaction was carried out at 60° C. for 4 hours. Then, the mixture was allowed to cool down to ambient temperature and 97.8g of acetic acid were added drop wise to the mixture while stirring. A dark red turbid viscous product was obtained with a pH (1%) of ~4.5-5.0, and a density of 1.12-1.18 g/cm³.

Of note, Silyl Compound no. 1 of Example 1 was used as obtained, therefore it contained some 1H,1H,2H-perfluoro-1-hexene (starting material of Example 1).

The obtained reaction mixture contained a mixture of oligomers with m being 1 or greater.

Figure 5:
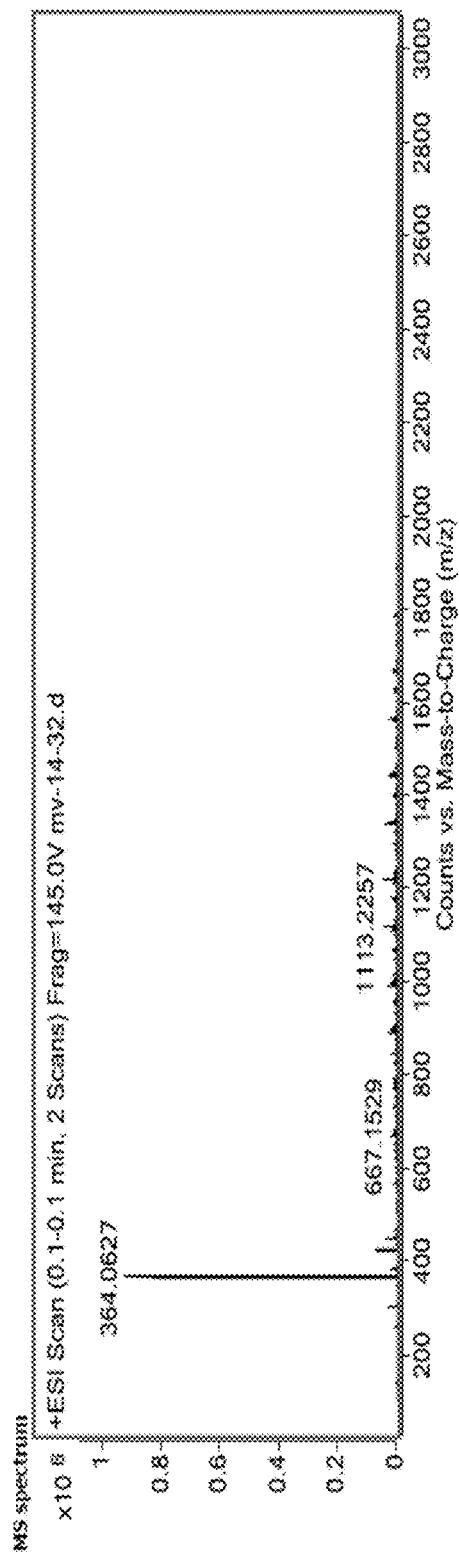
FIG. 5 shows the mass spectrum of Siloxane Oligomer A of the invention.

FIG. 5 shows the mass spectrum of the reaction product. The molecular weight of the oligomerized repeat unit molecule was slightly different from that of the corresponding monomer due to the hydrolyzation of ethoxy groups. More specifically, the hydrolyzed chain in the repeat unit lost three ethyl groups, but gained three hydrogen atoms (total molecular weight loss of 28×3 g/mol).

Siloxane Oligomer B

Siloxane Oligomer B was synthesized similarly to Siloxane Oligomer A, except that Silyl Compound 2 was used instead of Silyl Compound 1.

Siloxne Oligomer B

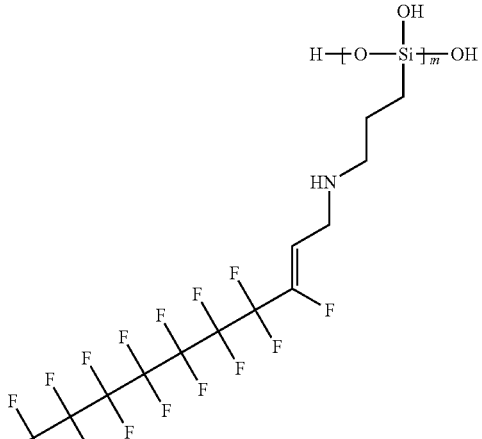

Siloxane Oligomer C

Siloxane Oligomer C was synthesized similarly to Siloxane Oligomer A, except that a second silyl compound was used together with Silyl Compound no. 1:

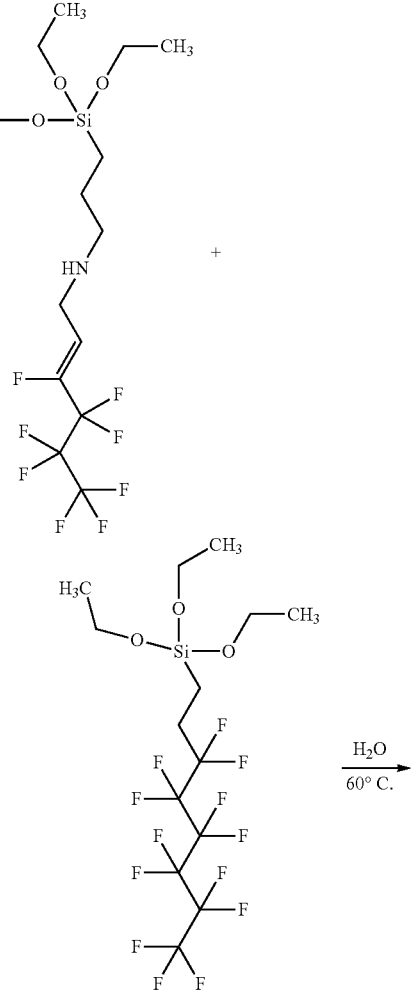

-continued

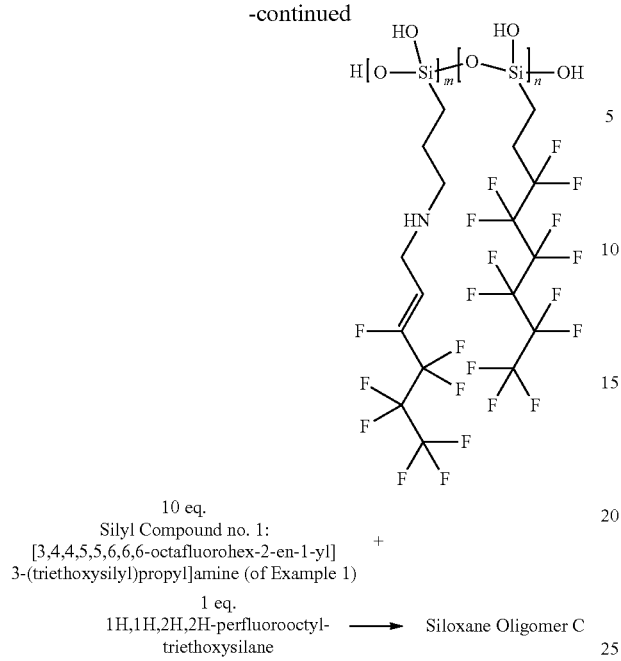

10 eq.
Silyl Compound no. 1:
[3,4,4,5,5,6,6,6-octafluorohex-2-en-1-yl]
3-(triethoxysilyl)propyl]amine (of Example 1)
+
1 eq.
1H,1H,2H,2H-perfluorooctyl-
triethoxysilane
→ Siloxane Oligomer C The obtained reaction mixture contained a mixture of oligomers with m and n each being 1 or greater.

Figure 6:
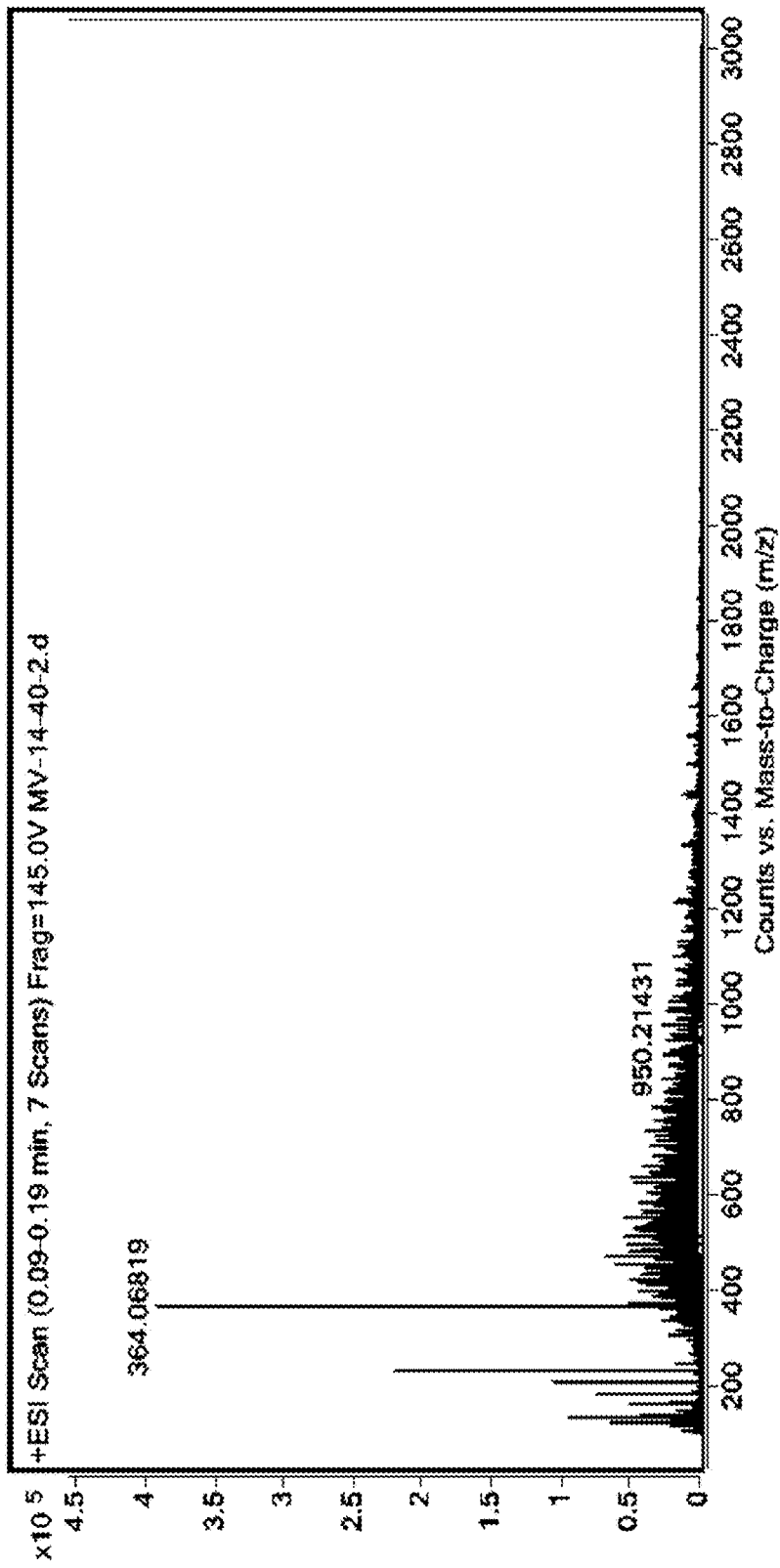
FIG. 6 shows the mass spectrum of Siloxane Oligomer C of the invention.

FIG. 6 shows the mass spectrum of the reaction product. Again, the molecular weight of the oligomerized repeat unit molecule was slightly different from that of the corresponding monomer due to the hydrolyzation of ethoxy groups.

In another manufacturing test, 763.3 g of Silyl compound no. 1 of Example 1, 75.2 g of 1H,1H,2H,2H perfluorooctyl triethoxysilane and 63.9 g DI water were added to the reactor, the hydrolysis reaction continued at 60° C. for 4 hours. Then, the mixture was allowed to cool down to ambient temperature. 880 g of a dark red product was obtained starting from 1 kg of raw materials (total weight of all of them).

Siloxane Oligomers $C^I$ and Following

Siloxane Oligomer C was also prepared using Silyl Compounds $1^I$ to $1^V$ above or using different acids for neutralization of the amine and/or different catalyst. More specifically:

Siloxane Oligomer CI was produced similarly to Siloxane Oligomer C except that Silyl Compound $1^I$ was used instead to Silyl Compound 1.

Siloxane Oligomer $C^{II}$ was produced similarly to Siloxane Oligomer C except that Silyl Compound $1^{II}$ was used instead to Silyl Compound 1.

Siloxane Oligomer $C^{III}$ was produced similarly to Siloxane Oligomer C except that Silyl Compound $1^{III}$ as used instead to Silyl Compound 1.

Siloxane Oligomer $C^{IV}$ was produced similarly to Siloxane Oligomer C except that Silyl Compound $1^{IV}$ was used instead to Silyl Compound 1.

Siloxane Oligomer $C^V$ was produced similarly to Siloxane Oligomer C except that Silyl Compound $1^V$ was used instead to Silyl Compound 1.

Siloxane Oligomer $C^{VI}$ was produced similarly to Siloxane Oligomer C except that formic acid was used instead of acetic acid.

Siloxane Oligomer $C^{VII}$ was produced similarly to Siloxane Oligomer C except that methanesulfonic acid was used instead of acetic acid.

Siloxane Oligomer D

Siloxane Oligomer D was produced similarly to Siloxane Oligomer C except that Silyl Compound 2 was used instead of Silyl Compound 1.

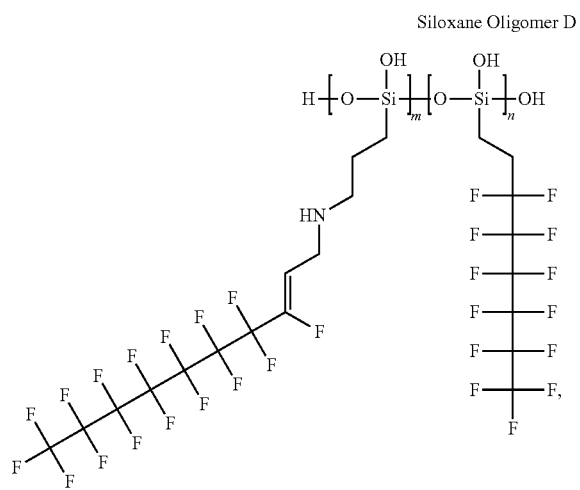

Siloxane Oligomer D

Siloxane Oligomer E

Siloxane Oligomer E was produced similarly to Siloxane Oligomer C except that Silyl Compound 3 was used instead of Silyl compound 1.

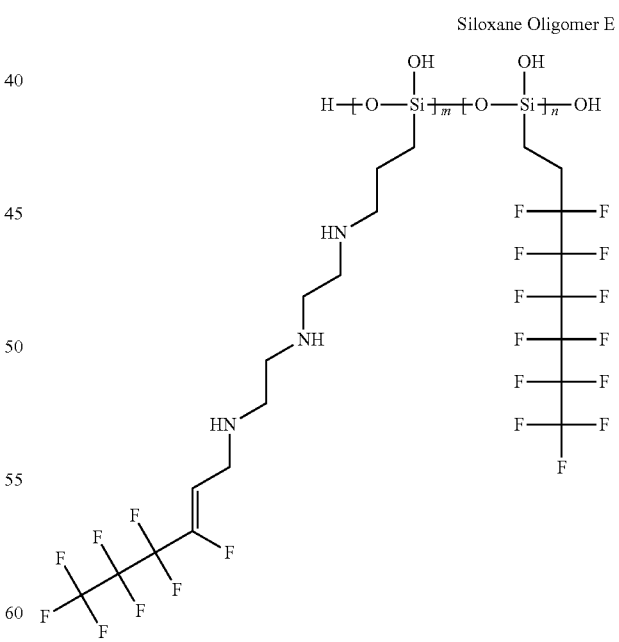

Siloxane Oligomer E

Siloxane Oligomer F

Siloxane Oligomer F was produced similarly to Siloxane Oligomer C except that Silyl Compound 4 was used instead of Silyl compound 1.

Siloxane Oligomer F

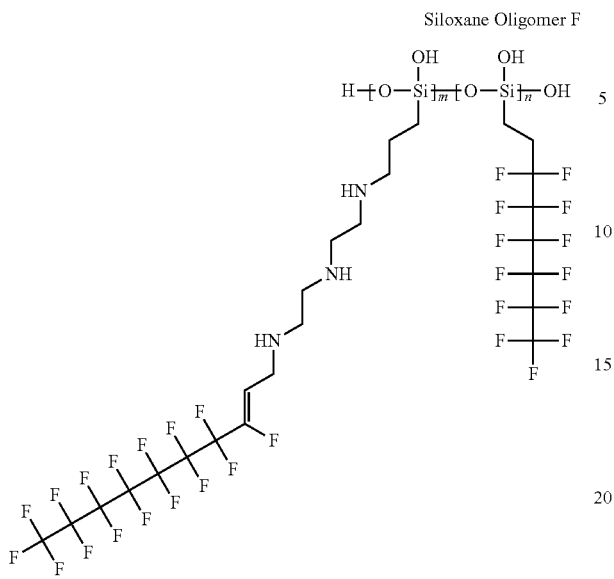

This compound exhibited low solubility in water.

Siloxane Oligomer G

Siloxane Oligomer G was produced similarly to Siloxane Oligomer C except that Silyl Compound 3 was used instead of Silyl compound 1 and triethoxy(octyl)silane was used instead of 1H,1H,2H,2H-perfluorooctyltriethoxysilane.

Siloxane Oligomer G

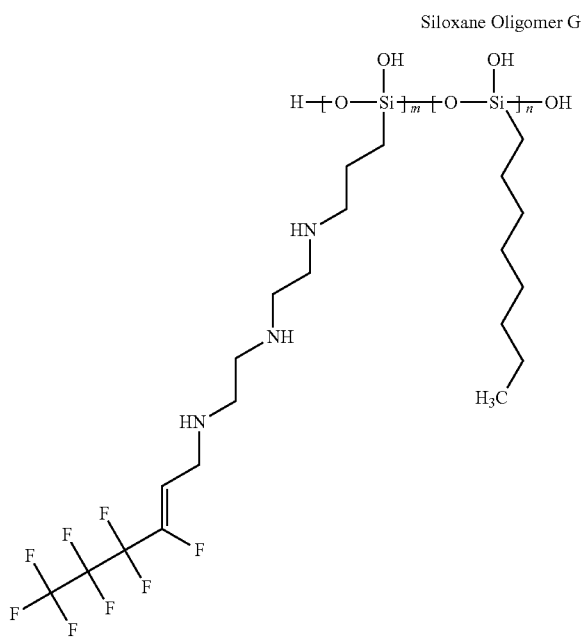

Siloxane Oligomer H

Siloxane Oligomer H was produced similarly to Siloxane Oligomer C except 1H,1H,2H,2H-perfluorodecyltriethoxysilane was used instead of 1H,1H,2H,2H-perfluorooctyltriethoxysilane.

Siloxane Oligomer H

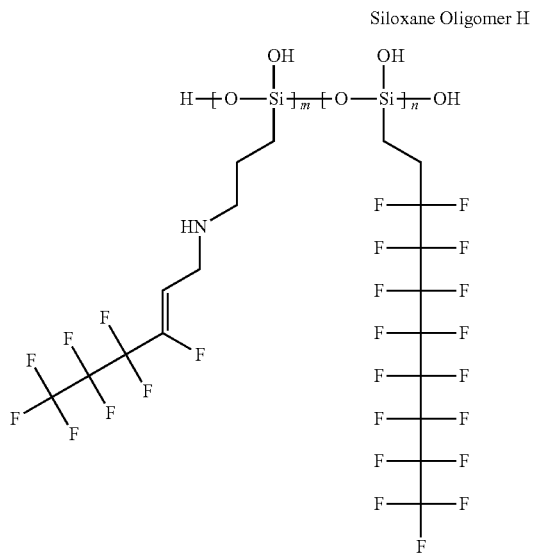

Example 3

Treatment of Porous and Non-Porous Surfaces

The siloxanes oligomers of the invention were used as a surface treatment on different substrates. To this end, the reaction mixtures obtained in Example 2 were separately diluted with water to obtain aqueous solutions containing 1% w/w of the corresponding siloxane oligomer (percentage based on the total weight of the solution).

Evonik's Dynasylan® F8815 (CAS no. 1011795.61.1) is one of a very limited number of commercially available water-born fluorosilane oligomers with both hydrophobic and lipophobic effects when applied on the surface of different substrates. It was used as a comparative. Dynasylan® F8815 was diluted with water to obtain an aqueous solution comprising 1.5% w/w of active.

The surfaces treated were:
microscope slides made of glass;
Sontara® AC: a fabric containing 55% polyester and 45% cellulose;
aluminum;
wood (white birch); and
concrete.

The surfaces were treated as follows. For the fabric, the samples were wetted with the products and dried at 100° C. for minutes. For glass, a droplet of diluted product was deposited on the surface. The droplet started to move and did not stop until all available surface was treated. For wood and concrete, the target surface was completely wetted with the diluted product.

The contact angles of water and mineral oil were measured for each of the treated surfaces. Static contact angle measurements were carried out on a Biolin® scientific instrument model Theta with automatic deposition of 5 ul of water (or mineral oil), 60 second measurements, one frame per 0.9 second. Five spots per slide and 3 slides per sample were measured. The reported values are obtained from calculating the average at 30st second. The results for are shown in the table below.

TABLE 6

| Substrate | | Glass | Fabric | Aluminum | Wood |
|---|---|---|---|---|---|
| Contact angle water (°) | No surface treatment | <5° | Water is absorbed | 67° | Water is absorbed |
| | Dynasylan ® F8815 | 62.5° | 130.8° | 99.3° | 115° |
| | Siloxane Oligomer A | 98° | | | |
| | Siloxane Oligomer B | 102° | | | |
| | Siloxane Oligomer C | 105° | 141.6° | 88° | 112.1° |
| | Siloxane Oligomer $C^I$ | 105° | | | |
| | Siloxane Oligomer $C^{II}$ | 106° | | | |
| | Siloxane Oligomer $C^{III}$ | 104° | | | |
| | Siloxane Oligomer D | 110° | | | |
| | Siloxane Oligomer E | 105° | | | |
| | Siloxane Oligomer G | 95° | | | |
| | Siloxane Oligomer H | 111° | | | |
| Contact angle mineral oil (°) | No surface treatment | <5° | Oil is absorbed | <5° | Oil is absorbed |
| | Dynasylan ® F8815 | 30.3° | 139.6° | 49.8° | 95° |
| | Siloxane Oligomer C | 63.8° | 118.5° | 58.9° | 80° |

Glass. As can be seen in the above table, while both Dynasylan® F8815 and Oligomer C increased the hydrophobicity and lipophobicity of the glass substrate, Oligomer C was more performant in that regard yielding much higher contact angles. It was observed that the observed lipophobic and hydrophobic effects of both Dynasylan® F8815 and Oligomer C appeared to be permanent as the products could not be washed off the glass surface.

Fabric. Oligomer C was slightly more performant for increasing hydrophobicity of the fabric, while Dynasylan® F8815 was slightly more performant for increasing lipophobicity of the fabric.

Aluminum. Both Dynasylan® F8815 and Oligomer C increased the hydrophobicity and lipophobicity of the glass substrate. Oligomer C was slightly more performant for increasing lipophobicity, while Dynasylan® F8815 was slightly more performant for increasing hydrophobicity.

Wood. Oligomer C and Dynasylan® F8815 caused similar increases in the hydrophobicity of the wood surface, while Dynasylan® F8815 was slightly more performant in increasing the lipophobicity of the wood.

Figure 7A:
FIG. 7A) shows water droplets on a concrete surface treated with Oligomer C of the invention, viewed from the top.
Figure 7B:
FIG. 7B) shows water droplets on a concrete surface treated with Dynasylan® F8815, viewed from the top.
Figure 8A:
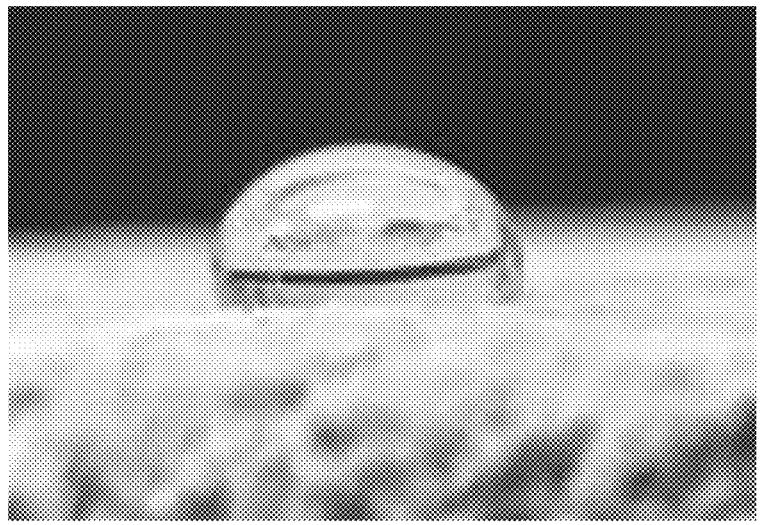
FIG. 8A) shows a mineral oil droplet on a concrete surface treated with Oligomer C of the invention, viewed from the side.
Figure 8B:
FIG. 8B) shows a mineral oil droplet on a concrete surface treated with Dynasylan® F8815, viewed from the side.
Figure 9A:
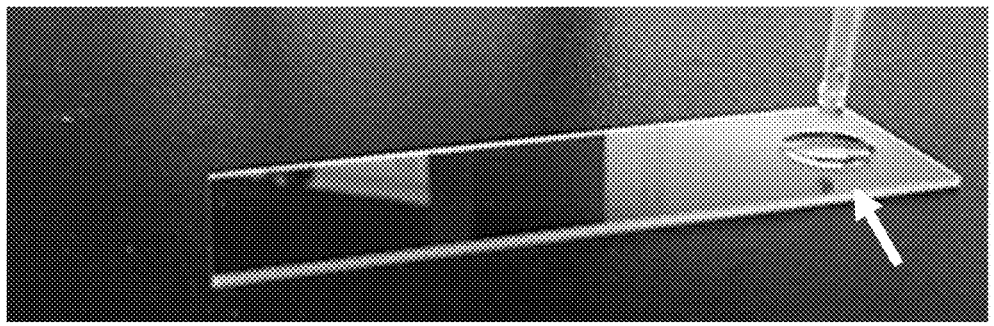
FIG. 9A) shows a droplet of an oligomer of the invention (indicated by a white arrow) self-propelling across a glass surface: the droplet is deposited at t=0 sec at the right end of a microscope slide lying horizontally.
Figure 9B:
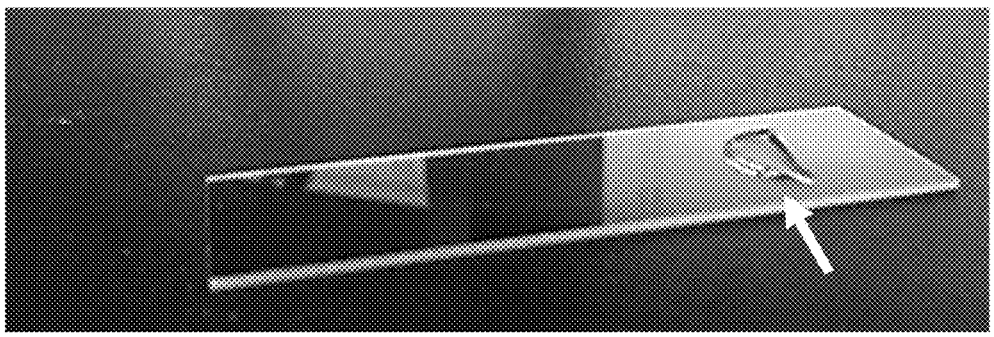
FIG. 9B) shows a droplet of an oligomer of the invention (indicated by a white arrow) self-propelling across a glass surface: droplet moving by self-propulsion toward the left at t=1 sec.
Figure 9C:
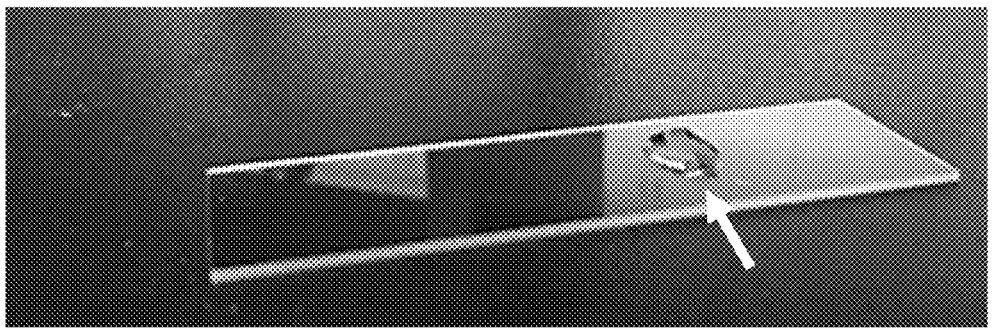
FIG. 9C) shows a droplet of an oligomer of the invention (indicated by a white arrow) self-propelling across a glass surface: droplet moving by self-propulsion toward the left at t=2 sec.
Figure 9D:
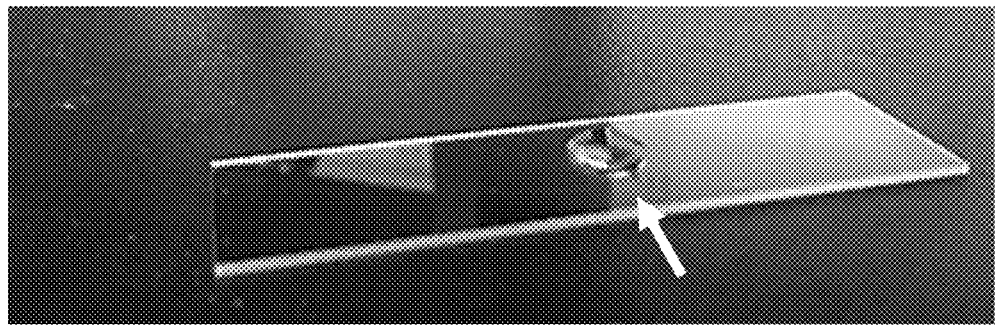
FIG. 9D) shows a droplet of an oligomer of the invention (indicated by a white arrow) self-propelling across a glass surface: droplet moving by self-propulsion toward the left at t=3 sec.
Figure 9E:
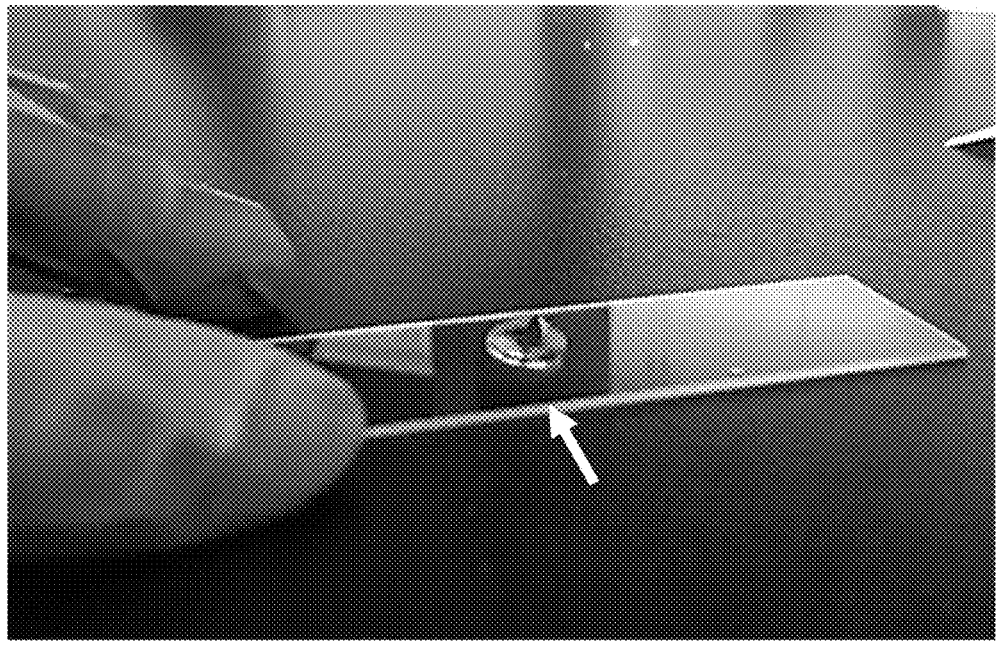
FIG. 9E) shows a droplet of an oligomer of the invention (indicated by a white arrow) self-propelling across a glass surface: droplet still moving by self-propulsion toward the left at t=4 sec, at this point, the experimenter lifted the left end of the microscope slide.
Figure 9F:
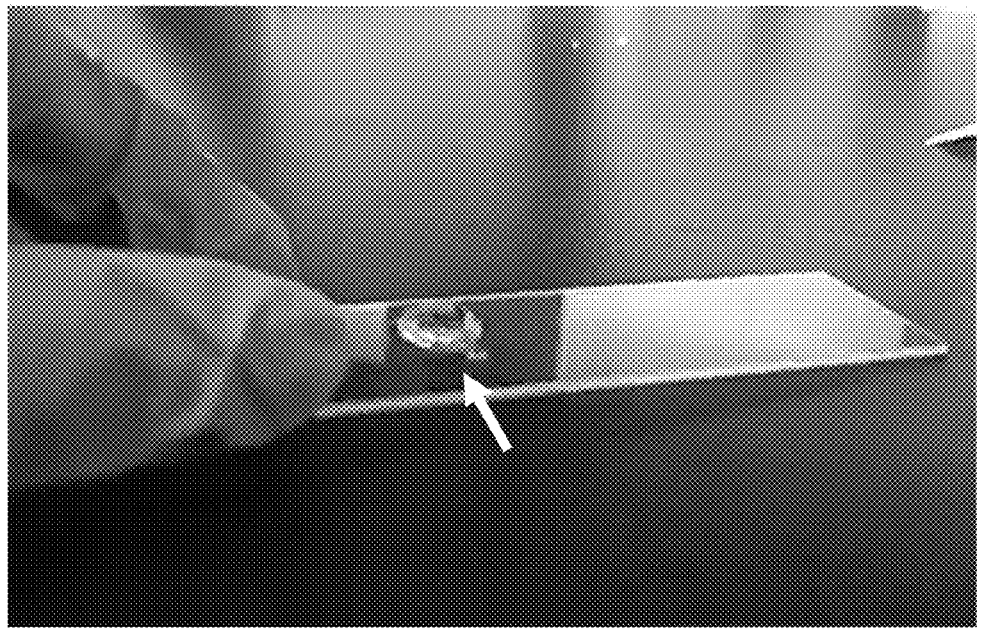
FIG. 9F) shows a droplet of an oligomer of the invention (indicated by a white arrow) self-propelling across a glass surface: the droplet continues moving by self-propulsion toward the left, now against the gravitational force, at t=5 sec.
Figure 9G:
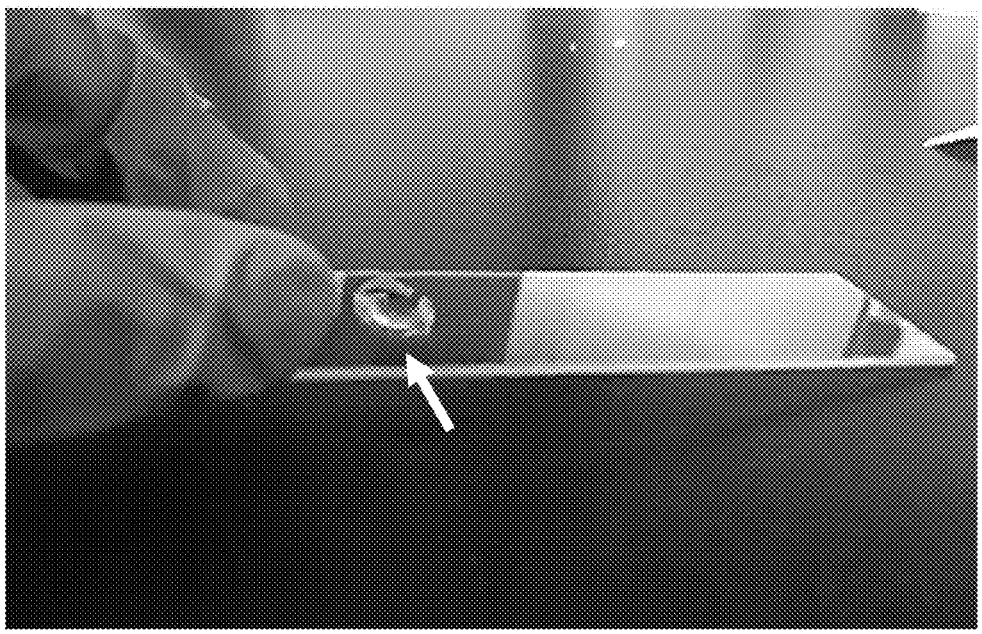
FIG. 9G) shows a droplet of an oligomer of the invention (indicated by a white arrow) self-propelling across a glass surface: the droplet continues moving by self-propulsion toward the left, now against the gravitational force, at t=6 sec.
Figure 9H:
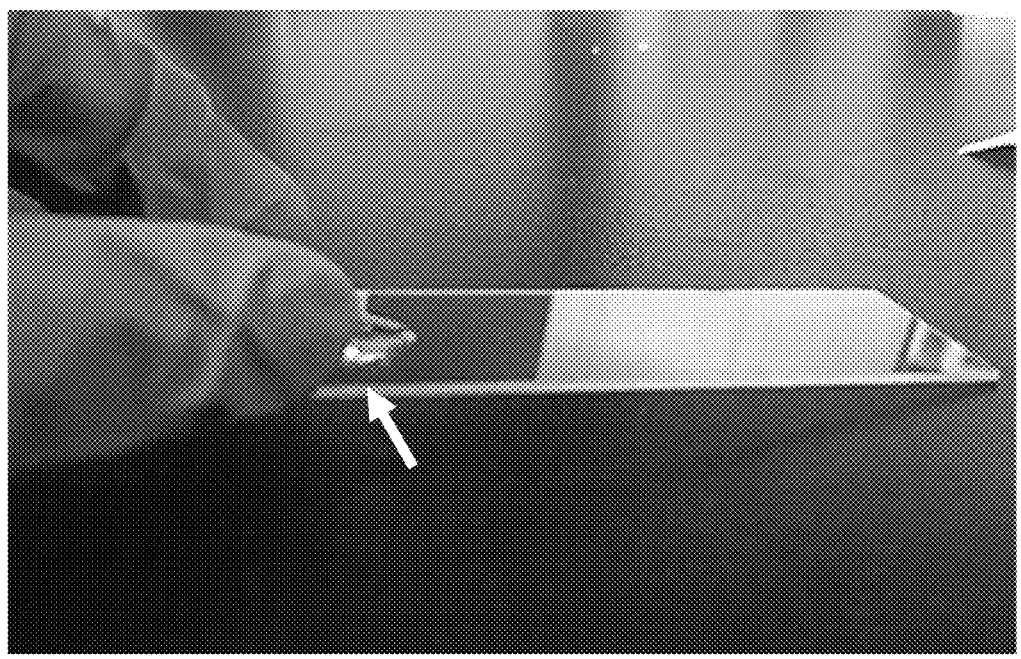
FIG. 9H) shows a droplet of an oligomer of the invention (indicated by a white arrow) self-propelling across a glass surface: the droplet continues moving by self-propulsion toward the left, now against the gravitational force, at t=7 sec.

Concrete. Experimental limitations prevented the measure of the contact angle on concrete. FIG. 7 shows water droplets on a concrete surface treated with A) Siloxane Oligomer C and B) Dynasylan® F8815 (viewed from the top). Both surfaces showed high hydrophobicity. The water droplets quickly ran off the treated substrates when they were inclined. FIG. 8 shows a mineral oil droplet on a concrete surface treated with A) Siloxane Oligomer C and B) Dynasylan® F8815 (viewed from the side). Both surfaces showed high lipophobicity.

Example 4

Self-Propulsion

Self-propulsion was observed for droplets of 1% aqueous solutions of Siloxane Oligomers B, C, $C^I$, $CH^{II}$, $C^{III}$, D, E, and H on glass substrates (microscope slides, without any previous surface treatment). The droplets exhibited self-propelled behavior on glass with a velocity between 0.1 to 1.0 cm/s.

As an example, FIG. 9 A) to H) are frames extracted from a video showing a droplet of Siloxane Oligomer C self-propelling across an untreated glass surface (microscope slide). First, in FIG. 9 A), at t=0 second, the droplet is deposited at the right end of a microscope slide lying horizontally. The droplets immediately start self-propelling toward the left. FIG. 9 B) to D) show the droplet at t=1, 2, and 3 seconds, respectively. In FIG. 9 D), taken at t=4 seconds, the droplet is still moving toward the left. Furthermore, at that point in time, the experimenter lifted the left end of the microscope slide forcing the droplet to move against the gravitational force. FIG. 9 F) to H) show the droplet continuing moving toward the left, against the gravitational force, at t=5, 6, and 7 seconds, respectively. For clarity, the position of the droplet is indicated by a white arrow on FIG. 9 A) to H).

It was observed that the droplets moved on the glass surface and changed the surface contact angle instantly. The contact angles of water and mineral oil after exposure to the aqueous solutions were as reported in the above table (compared to <5° beforehand).

In contrast, no self-propulsion was observed for the Dynasylan® F8815 aqueous solution (1.5%).

Example 5

Effect of the Solution Concentration

To study the effect of concentration, we measured the contact angle of water on a glass surface, a fabric surface (70% polyester and 30% cotton) and a concrete surface treated with aqueous solutions of Siloxane Oligomer C of various concentrations. We also determined whether the solutions self-propelled on glass. The surface treatment and measurements were as described in the previous examples. The results are reported in the table below.

TABLE 7

| Concentration | Water solubility | Water Contact Angle on Glass | Water Contact Angle on fabric | Water Contact Angle on concrete | Self-Propulsion on glass |
|---|---|---|---|---|---|
| 4.0% | Slight precipitation | | | 151.55° | Not present |
| 3.0% | Slight precipitation | 110° | 145° | 155.3° | Not present |

TABLE 7-continued

| Concentration | Water solubility | Water Contact Angle on Glass | Water Contact Angle on fabric | Water Contact Angle on concrete | Self-Propulsion on glass |
|---|---|---|---|---|---|
| 2.0% | Slight precipitation | 111.9° | 147.6° | 151.8° | Not present |
| 1.5% | Soluble | | 158.6° | 152.8° | |
| 1.0% | Soluble | 105.2° | 156° | 138.1° | Observed |
| 0.7% | Soluble | 109.4° | | | Observed |
| 0.5% | Soluble | 104.6° | 157.9° | 130.0° | Observed |
| 0.3% | Soluble | 94.1° | | | Observed |
| 0.1% | Soluble | 79.3° | No effect | No effect | Observed |

It was observed that self-propulsion speed increased with decreasing concentrations.

Example 6

Effect of the Molar Ratios of the Repeat Unit

A series of siloxane oligomers (Siloxane Oligomer $C^X$ to $C^{XIV}$) was produced similarly to Siloxane Oligomer C except that we varied the ratio of Silyl Compound no. 1 to 1H,1H,2H,2H-perfluorooctyltriethoxysilane (moral ratio α). We measured the contact angle of water (and in some cases mineral oil) on glass surfaces treated with 1% solutions of these siloxane oligomers. We also determined if the solutions self-propelled on glass. The surface treatment and measurements were as described in the previous examples. The results are reported in the table below.

TABLE 8

| Siloxane Oligomer | Molar Ratio α | Contact Angle Water (°) | Contact Angle Mineral Oil (°) | Self-Propulsion |
|---|---|---|---|---|
| Siloxane Oligomer $C^X$ | 10:0.3 | 75° | | Observed |
| Siloxane Oligomer $C^{XI}$ | 10:0.5 | 81° | | Observed |
| Siloxane Oligomer C | 10:1.0 | 105° | 63.8° | Observed |
| Siloxane Oligomer $C^{XII}$ | 10:1.4 | 102° | | Observed |
| Siloxane Oligomer $C^{XIII}$ | 10:2.7 | 109° | | Observed |
| Siloxane Oligomer $C^{XIV}$ | 10:4.3 | 111° | 80° | Observed |

The scope of the claims should not be limited by the preferred embodiments set forth in the examples, but should be given the broadest interpretation consistent with the description as a whole.

REFERENCES

The present description refers to a number of documents, the content of which is herein incorporated by reference in their entirety. These documents include, but are not limited to, the following:

Bain, Colin D., Graham D. Burnett-Hall, and Richard R. Montgomerie. "Rapid motion of liquid drops." Nature 372.6505 (1994): 414.
Chakraborty, Monojit, et al. "Thermally enhanced self-propelled droplet motion on gradient surfaces." RSC Advances 5.56 (2015): 45266-45275.
Chaudhury, Manoj K., and George M. Whitesides. How to make water run uphill. No. TR-48. HARVARD UNIV CAMBRIDGE MA DEPT OF CHEMISTRY, 1992.
Dos Santos, Fabrice Domingues, and Thierry Ondarcuhu. "Free-running droplets." Physical Review Letters 75.16 (1995): 2972.
Izri, Ziane, et al. "Self-propulsion of pure water droplets by spontaneous marangoni-stress-driven motion." Physical review letters 113.24 (2014): 248302.
Sumino, Yutaka, and Kenichi Yoshikawa. "Self-motion of an oil droplet: A simple physicochemical model of active Brownian motion." Chaos: An Interdisciplinary Journal of Nonlinear Science 18.2 (2008): 026106.
Yao, Xi, et al. "Running droplet of interfacial chemical reaction flow." Soft Matter 8.22 (2012): 59885991.
Product Information Dynasylan® F 8815, Brochure by Evonik Resource GmbH, dated August 2016
Dynasylan® Product Range, Brochure by Evonik Industries, revised 1 July 2016
CAS entry no. 1011795.61.1-Dynasylan® F 8815
EP patent 1 178 071 B1
EP patent application 0 675 128 A1
International patent application WO 2005/014741 A1
International patent application WO 2006/010388 A1
International patent application WO 2006/010666 A1
International patent application WO 2010/114111 A1
U.S. Pat. No. 5,849,942
U.S. Pat. No. 5,885,341
U.S. Pat. No. 6,251,989
U.S. Pat. No. 6,491,838
U.S. Pat. No. 6,706,923
U.S. Pat. No. 8,298,679
U.S. Pat. No. 8,349,911
US patent application 2009/0198000 A1
US patent application 2016/0244638 A1

The invention claimed is:

1. A siloxane oligomer of formula:

$$\begin{array}{c} \text{OH} \quad\quad\quad \text{OH} \\ | \quad\quad\quad\quad | \\ -\!\!\!-\!\!\!\left[\text{Si}-\text{O}\right]_m\!\!\left[\text{Si}-\text{O}\right]_n\!\!-\!\!\!- \\ | \quad\quad\quad\quad | \\ R^1 \quad\quad\quad R^{10} \\ | \\ \text{NH} \\ | \\ R^2 \\ \diagdown \\ \text{CH} \\ \| \\ CR^3 \\ \diagdown \\ R^4 \end{array}$$

wherein:
R$^1$ is alkylene optionally interrupted with one or more —NR$^{20}$-group;
R$^2$ is alkylene;
R$^3$ is —H, —F or optionally substituted alkyl;
R$^4$ is alkyl or fluoroalkyl;
R$^{10}$ is fluoroaryl or alkyl optionally substituted, preferably end-substituted, by:

fluoroalkyl,
glycidyloxy,
optionally substituted aryl,
optionally substituted aryloxy, or
—N⁺(R²¹)(R²²)(R²³);
R²⁰ is H or alkyl;
R²¹, R²² and R²³ are independently alkyl, optionally substituted aryl, or alkyl-O-alkyl; and
m and n represent the number of repeat units, m being 1 or greater and n being 0 or greater.

2. The oligomer of claim 1, wherein n is 0.
3. The oligomer of claim 1, wherein $R^1$ is uninterrupted alkylene or alkylene interrupted by one or two —NR²⁰—.
4. The oligomer of claim 3, wherein $R^1$ is -propylene- or *-propylene-NH-ethylene-NH-ethylene-, the star indicating the point of attachment to the Si atom.
5. The oligomer of claim 1, wherein $R^2$ is a $C_{1-6}$ alkylene.
6. The oligomer of claim 5, wherein $R^2$ is methylene.
7. The oligomer of claim 1, wherein $R^3$ is —F.
8. The oligomer of claim 1, wherein $R^4$ is a perfluoroalkyl.
9. The oligomer of claim 8, wherein $R^4$ is $C_3$ perfluoroalkyl or $C_7$ perfluoroalkyl.
10. The oligomer of claim 1, wherein n is 1 or greater.
11. The oligomer of claim 10, wherein $R_{10}$ is unsubstituted alkyl or alkyl end-substituted with fluoroalkyl.
12. The oligomer of claim 11, wherein $R_{10}$ is unsubstituted alkyl or alkyl end-substituted with perfluoroalkyl.
13. The oligomer of claim 12, wherein the unsubstituted alkyl in $R^{10}$ is $C_{2-12}$alkyl.
14. The oligomer of claim 13, wherein the unsubstituted alkyl in $R^{10}$ is hexyl.
15. The oligomer of claim 12, wherein the alkyl end-substituted with perfluoroalkyl in $R^{10}$ is a $C_{1-6}$ alkyl.
16. The oligomer of claim 15, wherein the alkyl end-substituted with perfluoroalkyl in $R^{10}$ is ethyl.
17. The oligomer of claim 12, wherein the perfluoroalkyl end-substituting the alkyl in $R^{10}$ is a $C_{4-10}$ perfluoroalkyl.
18. The oligomer of claim 17, wherein the perfluoroalkyl end-substituting the alkyl in $R^{10}$ is a perfluorohexyl or perfluorooctyl.
19. The oligomer of claim 12, wherein $R^{10}$ is 1H,1H,2H,2H-perfluorooctyl, 1H,1H,2H,2H-perfluorodecyl, or octyl.
20. The oligomer of claim 1, being:

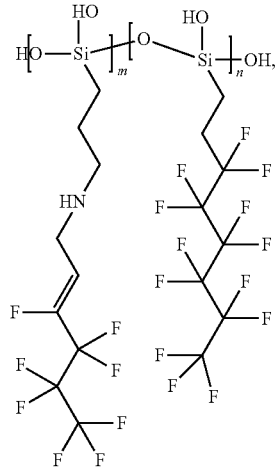
(Siloxane Oligomer A)

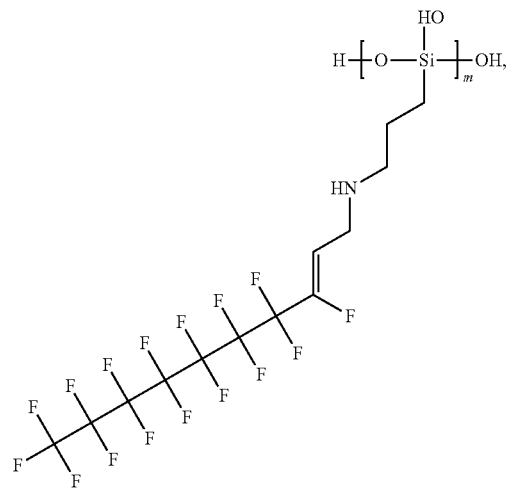
(Siloxane Oligomer B)

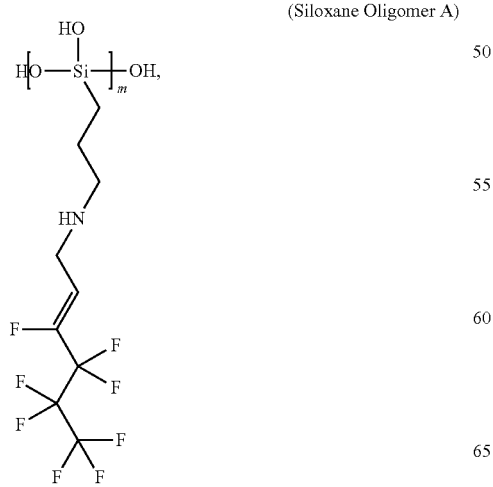
(Siloxane Oligomer C)

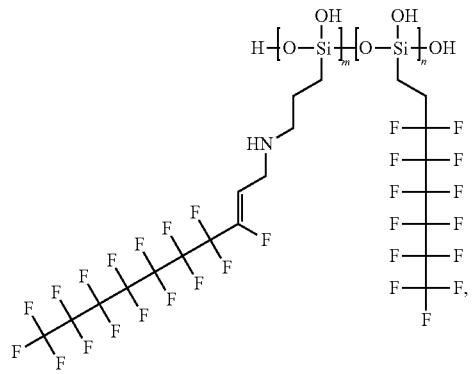
(Siloxane Oligomer D)

(Siloxane Oligomer E)
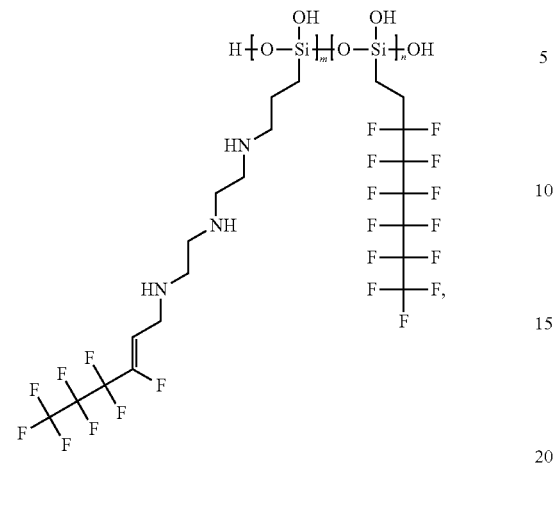
(Siloxane Oligomer G)
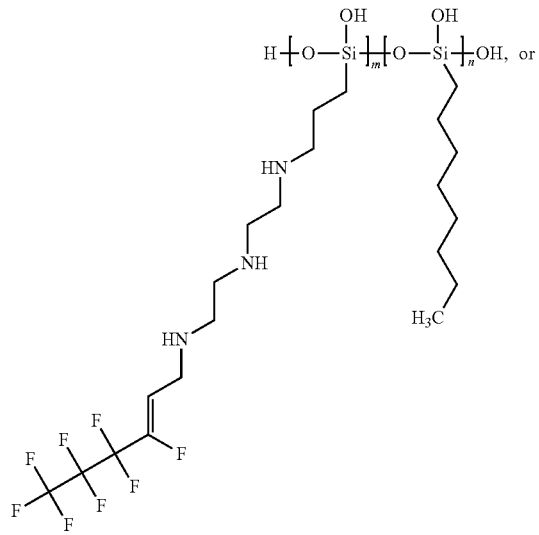
(Siloxane Oligomer F)
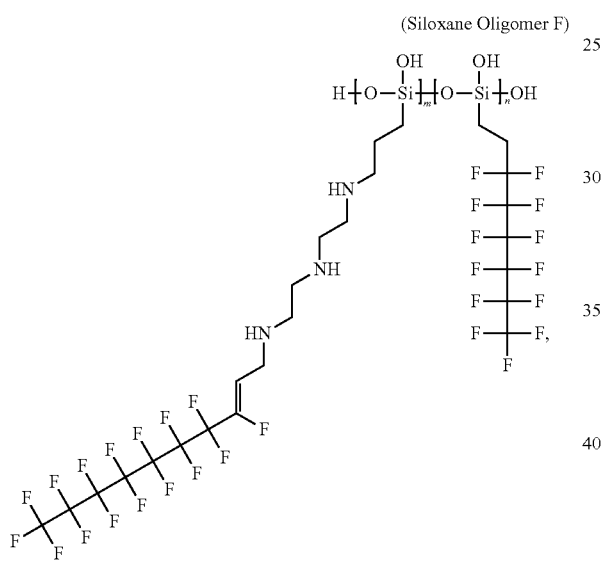
(Siloxane Oligomer H)
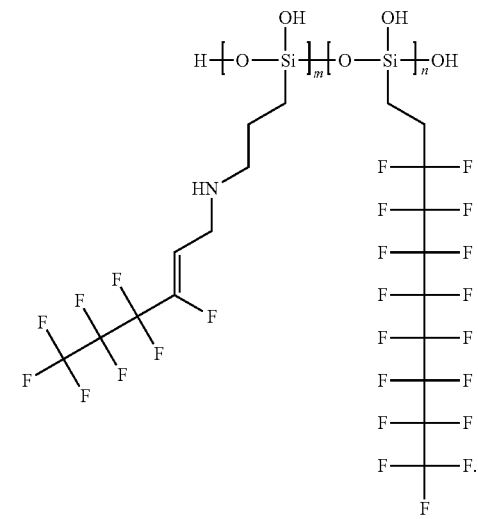
* * * * *